United States Patent
Shibasaki et al.

(10) Patent No.: US 11,370,883 B2
(45) Date of Patent: Jun. 28, 2022

(54) POLYCARBONATE RESIN COMPOSITION, MOLDED ARTICLE, POLYCARBONATE RESIN, AND END-CAPPING AGENT FOR POLYCARBONATE RESIN

(71) Applicant: MITSUBISHI GAS CHEMICAL COMPANY, INC., Tokyo (JP)

(72) Inventors: Yuji Shibasaki, Iwate (JP); Hiroyoshi Maruyama, Kanagawa (JP); Kimitaka Nakao, Kanagawa (JP); Yuusuke Nii, Ibaraki (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 137 days.

(21) Appl. No.: 16/615,685

(22) PCT Filed: Apr. 16, 2018

(86) PCT No.: PCT/JP2018/015639
§ 371 (c)(1),
(2) Date: Nov. 21, 2019

(87) PCT Pub. No.: WO2018/216396
PCT Pub. Date: Nov. 29, 2018

(65) Prior Publication Data
US 2020/0115496 A1 Apr. 16, 2020

(30) Foreign Application Priority Data
May 25, 2017 (JP) .............................. JP2017-103600

(51) Int. Cl.
| C08G 64/00 | (2006.01) |
| C08G 64/40 | (2006.01) |
| C07C 39/225 | (2006.01) |
| C08K 5/00 | (2006.01) |

(52) U.S. Cl.
CPC ............ *C08G 64/40* (2013.01); *C07C 39/225* (2013.01); *C08K 5/005* (2013.01); *C07C 2602/10* (2017.05)

(58) Field of Classification Search
CPC ....... C08G 64/40; C08L 69/00; C07C 39/225; C07C 2602/10
See application file for complete search history.

(56) References Cited

U.S. PATENT DOCUMENTS

| 4,469,860 A | 9/1984 | Rosenquist | |
| 2003/0065117 A1 | 4/2003 | Poreddy et al. | |
| 2013/0184406 A1* | 7/2013 | Miyazaki | C08G 73/1042 524/600 |

FOREIGN PATENT DOCUMENTS

| CN | 1558924 | 12/2004 |
| CN | 102453251 | 5/2012 |
| CN | 102844377 | 12/2012 |
| EP | 0834499 | 4/1998 |
| EP | 2098520 | 9/2009 |
| EP | 2 562 217 | 2/2013 |
| JP | H02-155922 | 6/1990 |
| JP | 9-302086 | 11/1997 |
| JP | 2002-080415 | 3/2002 |
| JP | 2002-302543 | 10/2002 |
| JP | 2012-103656 | 5/2012 |
| JP | 2014-051538 | 3/2014 |
| KR | 2013-0119639 | 11/2013 |
| WO | 01-066624 | 9/2001 |
| WO | 2010/086385 | 8/2010 |

OTHER PUBLICATIONS

Sofie Celen et al., "Synthesis and Biological Evaluation of 11C-Labeled beta-Galactosyl Triazoles as Potential PET Tracers for In Vivo LacZ Reporter Gene Imaging," 17 Bioorganic & Medicinal Chemistry 5117 (2009).*
English-language machine translation of JP2014051538, performed on Espacenet on Jul. 8, 2021, 31 pages.*
Extended European Search Report dated Mar. 3, 2020 in EP application No. 18805678.2.
Office Action dated Jul. 6, 2020 issued in corresponding European Patent Application No. 18 805 678.2.
https://pubchem.ncbi.nlm.nih.gov/compound/11425076#section=Substances.
Official Communication issued in International Patent Application No. PCT/JP2018/015639, dated Jul. 10, 2018 (ISR).
Official Communication issued in International Patent Application No. PCT/JP2018/015639, dated Jul. 10, 2018 (IPRP).

(Continued)

*Primary Examiner* — Nicholas E Hill
(74) *Attorney, Agent, or Firm* — Greenblum & Bernstein, P.L.C.

(57) ABSTRACT

A polycarbonate resin composition, a molded article, a polycarbonate resin, and an end-capping agent for polycarbonate resins are provided. The polycarbonate resin composition contains: a polycarbonate resin having a terminal structure represented by Formula (A) and having a viscosity average molecular weight from $1 \times 10^4$ to $5 \times 10^4$, and a stabilizer. In Formula (A), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

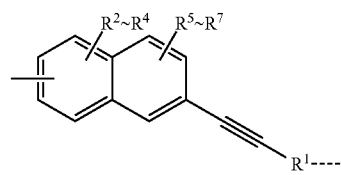

10 Claims, No Drawings

(56) References Cited

OTHER PUBLICATIONS

Chinese Office Action issued with respect to Chinese Application No. 201880033900.2, dated May 19, 2021.
Polymer Materials, 2016, pp. 23.
Ryo Irie et al., Asymmetric Aerobic Oxidative Coupling of 2-Naphthol Derivatives Catalyzed by Photo-Activated Chiral (NO)Ru(II)-Salen Complex, Synlett 2000, No. 10, 1433-1436.
The Research of Synthesis of Bisphenol a Polycarbonate by Melt Transesterification, 2012.
Kobunshi Ronbunshu, Takata, T., Synthesis and polymerization of cyclic carbonates containing a binapthyl moiety, vol. 54, No. 12, pp. 974-981, Dec. 1997.
Japanese Office Action issued with respect to Japanese Application No. 2017-103600, dated Jun. 15, 2021.
Chinese Office issued with respect to Chinese application No. 201880033900.2, dated Jan. 13, 2022.

* cited by examiner

POLYCARBONATE RESIN COMPOSITION, MOLDED ARTICLE, POLYCARBONATE RESIN, AND END-CAPPING AGENT FOR POLYCARBONATE RESIN

TECHNICAL FIELD

The present invention relates to a polycarbonate resin composition, a molded article, a polycarbonate resin, and an end-capping agent for polycarbonate resins.

BACKGROUND ART

Polycarbonate resins, represented by aromatic polycarbonate resins, are resins having excellent heat resistance, mechanical properties, and electrical properties, and are widely used in, for example, automotive materials, electrical and electronic device materials, various household electrical device materials, housing materials, and other materials for component production in industrial fields. In particular, flame-retardant aromatic polycarbonate resin compositions have been suitably used as members for office automation/information-processing equipment, such as a computer, a notebook computer, a mobile phone, a printer, a copying machine, or the like.

Typically, as a method for imparting flame retardancy to an aromatic polycarbonate resin, a halogen-based flame retardant or a phosphorus-based flame retardant is blended with the aromatic polycarbonate resin.

However, an aromatic polycarbonate resin composition containing a halogen-based flame retardant containing chlorine or bromine may often lead to degradation in thermal stability, or corrosion of a screw of the molding machine or a mold for molding during the molding process. In addition, the use of an aromatic polycarbonate resin composition containing a phosphorus-based flame retardant may be limited because high transparency, which is the characteristic of an aromatic polycarbonate resin, may be deteriorated, or impact resistance and heat resistance of the aromatic polycarbonate resin may be deteriorated. In addition, the halogen-based flame retardants and phosphorus-based flame retardants may cause environmental pollution during product disposal and collect. As such, there has been a demand to impart flame retardancy without using these flame retardants in recent years.

In such a circumstance, Patent Document 1 describes an aromatic polycarbonate resin composition containing, per (a) 100 parts by mass of an aromatic polycarbonate resin having a terminal structure represented by Formula (A) and having a viscosity average molecular weight of $1 \times 10^4$ to $5 \times 10^4$, (b) from 0.005 parts by mass to 0.1 parts by mass of a metal salt of an organic sulfonic acid.

[Chemical Formula 1]

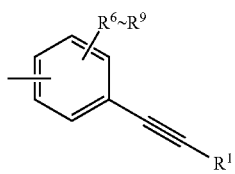

Formula (A)

In Formula (A), $R^1$ is selected from the group consisting of a hydrogen atom, halogen atoms, linear or branched alkyl groups having from 1 to 9 carbons, linear or branched alkenyl groups having from 2 to 9 carbons, linear or branched hydroxyalkyl groups having from 1 to 9 carbons, linear or branched hydroxyalkenyl groups having from 2 to 9 carbons, linear or branched haloalkyl groups having from 1 to 9 carbons, linear or branched haloalkenyl groups having from 2 to 9 carbons, and optionally substituted aryl groups having from 6 to 12 carbons. $R^6$ to $R^9$ are each independently selected from the group consisting of a hydrogen atom, alkyl groups having from 1 to 9 carbons, and oxyalkyl groups (alkoxy groups) having from 1 to 9 carbons.

CITATION LIST

Patent Documents

Patent Document 1: JP 2014-051538 A

SUMMARY OF INVENTION

Technical Problem

However, in recent years, demand for flame retardancy has grown increasingly, and it has been found that flame retardancy in the polycarbonate resin composition described in Patent Document 1 is insufficient. Furthermore, even when flame retardancy is high, if the heat resistance is poor, the use thereof is limited.

The present invention is to solve such problems, and an object of the present invention is to provide a polycarbonate resin composition having excellent flame retardancy and heat resistance, a molded article, a polycarbonate resin, and an end-capping agent for polycarbonate resins.

Solution to Problem

The inventors conducted a study for the object described above, and, it was found that the problems can be solved by making a terminal of a polycarbonate resin to be a specific structure. Specifically, the problems are solved by the following means <1>, <6>, and <9>, and preferably <2> to <5>, <7>, <8>, <10>, and <11>.

<1> A polycarbonate resin composition containing: a polycarbonate resin having a terminal structure represented by Formula (A) and having a viscosity average molecular weight of $1 \times 10^4$ to $5 \times 10^4$, and a stabilizer.

[Chemical Formula 2]

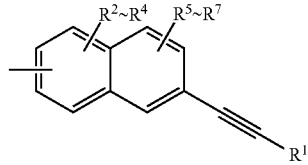

Formula (A)

In Formula (A), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

<2> The polycarbonate resin composition according to <1>, where Formula (A) is represented by Formula (B) below.

[Chemical Formula 3]

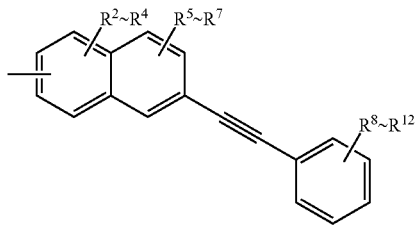

Formula (B)

In Formula (B), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

<3> The polycarbonate resin composition according to <1>, where Formula (A) is represented by Formula (C) below.

[Chemical Formula 4]

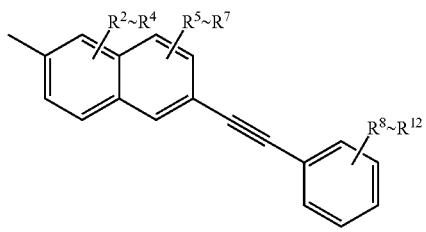

Formula (C)

In Formula (C), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

<4> The polycarbonate resin composition according to any one of <1> to <3>, where the stabilizer is at least one type selected from the group consisting of thermal stabilizers and antioxidants.

<5> A molded article formed from the polycarbonate resin composition described in any one of <1> to <4>.

<6> A polycarbonate resin having a terminal structure represented by Formula (A) and having a viscosity average molecular weight of $1 \times 10^4$ to $5 \times 10^4$.

[Chemical Formula 5]

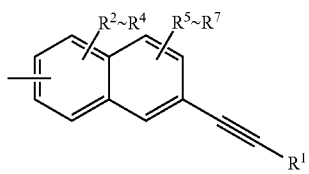

Formula (A)

In Formula (A), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

<7> The polycarbonate resin according to <6>, where Formula (A) is represented by Formula (B) below.

[Chemical Formula 6]

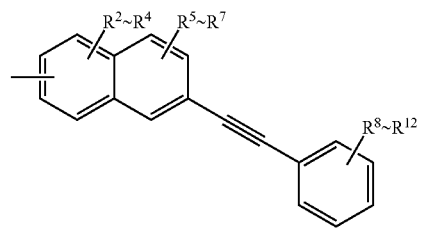

Formula (B)

In Formula (B), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

<8> The polycarbonate resin according to <1>, where Formula (A) is represented by Formula (C) below.

[Chemical Formula 7]

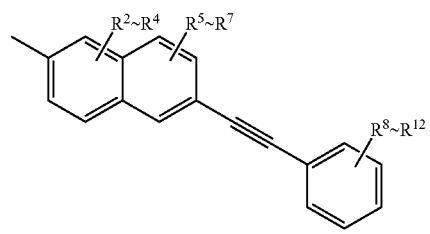

Formula (C)

In Formula (C), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

<9> An end-capping agent for a polycarbonate resin, the end-capping agent being represented by Formula (1) below.

[Chemical Formula 8]

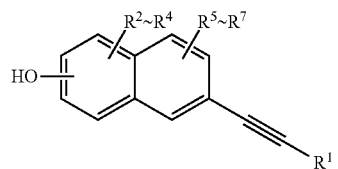

Formula (1)

In Formula (1), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

<10> The end-capping agent for a polycarbonate resin according to <9>, where Formula (1) is represented by Formula (2) below.

[Chemical Formula 9]

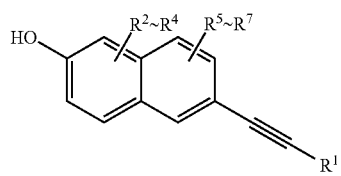

Formula (2)

In Formula (2), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

<11> The end-capping agent for a polycarbonate resin according to <9>, where Formula (1) is represented by Formula (3) below.

[Chemical Formula 10]

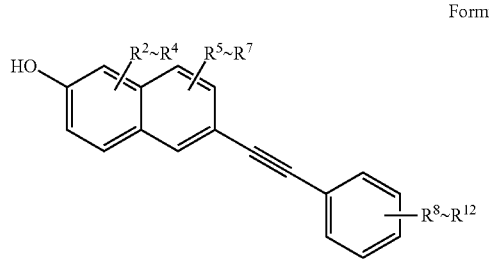

Formula (3)

In Formula (3), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

Advantageous Effects of Invention

The present invention can provide a polycarbonate resin composition having excellent flame retardancy and heat resistance, a molded article, a polycarbonate resin, and an end-capping agent for polycarbonate resins.

DESCRIPTION OF EMBODIMENTS

The contents of the present invention will be described in detail below. Note that, in the present specification, "(from) . . . to . . . " is used in a sense that includes the numerical values described before and after as the lower limit value and the upper limit value.

The polycarbonate resin composition according to an embodiment of the present invention is characterized by containing a polycarbonate resin having a terminal structure represented by Formula (A) and having a viscosity average molecular weight of $1\times10^4$ to $5\times10^4$, and a stabilizer. With such a configuration, a polycarbonate resin composition having excellent flame retardancy and heat resistance can be obtained.

[Chemical Formula 11]

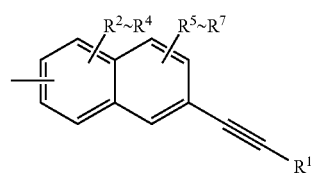

Formula (A)

In Formula (A), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

Note that, in Formula (A), regarding groups indicated as $R^2$ to $R^4$ and $R^5$ to $R^7$, each of the groups is bonded to a carbon atom constituting the ring structure of the naphthalene ring at any position thereof. That is, there are 10 carbon atoms constituting the ring structure of the naphthalene ring, in which one of the carbon atoms is bonded to the group including—carbon-carbon triple bond-$R^1$, another one of the carbon atoms is bonded to the main chain of the polycarbonate resin, and, among the rest of the carbon atoms, other five carbon atoms each having a hydrogen atom as a substituent have groups represented by $R^2$ to $R^7$. The same applies to the formulas below.

In Formula (A), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons. The alkyl group, the alkenyl, and the aryl group may contain a substituent but preferably contain no substituent. The substituent that may be contained in the alkyl group, the alkenyl group, and the aryl group is selected from the group consisting of halogen atoms, a hydroxyl group, alkyl groups having from 1 to 9 carbons, and alkoxy groups having from 1 to 9 carbons. As the substituent of the alkyl group and the alkenyl group, a halogen atom and a hydroxyl group are preferred. As the substituent of the aryl group, an alkyl group having from 1 to 4 carbons is preferred, and a methyl group is more preferred.

$R^1$ is preferably a hydrogen atom, a methyl group, an ethyl group, and a phenyl group, and more preferably a hydrogen atom and an unsubstituted phenyl group.

In Formula (A), $R^2$ to $R^7$ are each independently preferably a hydrogen atom or an alkyl group having from 1 to 9 carbons, more preferably a hydrogen atom or an alkyl group having from 1 to 4 carbons, and even more preferably a hydrogen atom.

The polycarbonate resin composition according to an embodiment of the present invention promotes a cyclization reaction of the terminal triple bond groups by heat during the combustion, therefore can impart excellent flame retardancy and heat resistance to a molded article. As the position at which the triple bond group is included in the structure of the polycarbonate resin, besides the terminal group, a structure, in which the triple bond is copolymerized in the molecular chain of the polycarbonate resin, may be contemplated. However, in the case where a triple bond group is included in the molecular chain, the glass transition temperature (Tg) might decrease, and reduction of heat resistance of a molded article might occur. Furthermore, in an embodiment of the present invention, the polycarbonate resin composition including a carbon-carbon triple bond at the terminal group allows cyclization reaction to proceed among the terminal groups due to heat during combustion, thus promotes formation of a carbonized layer during the combustion process. Therefore, it is expected that flame retardancy can be exerted more effectively than a case of a structure containing a triple bond in a molecular chain.

In the polycarbonate resin used in an embodiment of the present invention, Formula (A) is preferably represented by Formula (B) below.

[Chemical Formula 12]

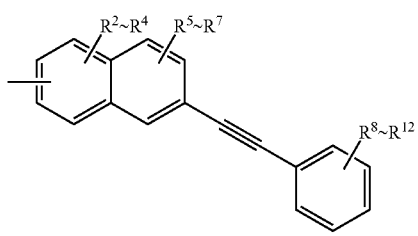

Formula (B)

In Formula (B), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

[Chemical Formula 14]

In Formula (B), $R^2$ to $R^7$ are synonymous with $R^2$ to $R^7$ in Formula (A), and preferable ranges are also the same.

In Formula (B), $R^8$ to $R^{12}$ are each independently preferably a hydrogen atom, an alkyl group having from 1 to 4 carbons (e.g. a methyl group or ethyl group) or an alkoxy group having from 1 to 4 carbons (e.g. a methoxy group or ethoxy group), more preferably a hydrogen atom or an alkyl group having from 1 to 4 carbons, and even more preferably a hydrogen atom.

The polycarbonate resin used in an embodiment of the present invention is preferably a polycarbonate resin having a phenylethynylnaphthyl group and an ethynylnaphthyl group in the terminal structure represented by Formula (A), and more preferably a polycarbonate resin having a phenylethynylnaphthyl group at a terminal end. The naphthyl group included in the phenylethynylnaphthyl group and the ethynylnaphthyl group is preferably bonded to an ethynyl group at the 6-position and bonded to a polycarbonate resin (preferably a carbonate group of the polycarbonate resin) at the 2-position.

More specifically, in the polycarbonate resin used in an embodiment of the present invention, Formula (A) is preferably represented by Formula (C).

[Chemical Formula 13]

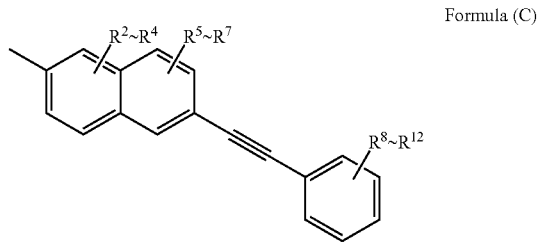

Formula (C)

In Formula (C), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

In Formula (C), $R^2$ to $R^7$ are synonymous with $R^2$ to $R^7$ in Formula (A), and preferable ranges are also the same.

In Formula (C), $R^8$ to $R^{12}$ are synonymous with $R^8$ to $R^{12}$ in Formula (B), and preferable ranges are also the same.

The polycarbonate resin used in an embodiment of the present invention is more preferably a polycarbonate resin represented by Formula (I) below.

Formula (I)

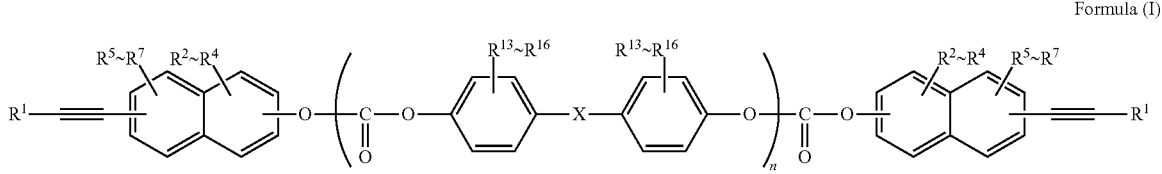

In Formula (I), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; $R^2$ to $R^7$ are each independently selected from the group consisting of a hydrogen atom, alkyl groups having from 1 to 9 carbons, and alkoxy groups having from 1 to 9 carbons; $R^{13}$ to $R^{16}$ are each independently selected from the group consisting of a hydrogen atom, a fluorine atom, a chlorine atom, a bromine atom, an iodine atom, alkyl groups having from 1 to 9 carbons, alkoxy groups having from 1 to 5 carbons, aryl groups having from 6 to 12 carbons, alkenyl groups having from 2 to 5 carbons, and aralkyl groups having from 7 to 17 carbons; and n is an integer of 15 to 200. X is selected from Formulas (I-1) below.

Formulas (I-1)

[Chemical Formula 15]

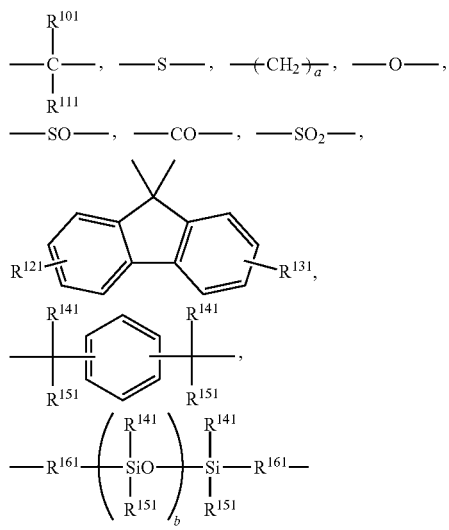

In Formulas (I-1), $R^{101}$ and $R^{111}$ are each independently selected from the group consisting of a hydrogen atom, a fluorine atom, a chlorine atom, a bromine atom, an iodine atom, alkyl groups having from 1 to 9 carbons, alkoxy groups having from 1 to 5 carbons, aryl groups having from 6 to 12 carbons, alkenyl groups having from 2 to 5 carbons, and aralkyl groups having from 7 to 17 carbons; $R^{101}$ and $R^{111}$ may be bonded to each other to form an aromatic ring, an aliphatic ring, or a heterocyclic ring; $R^{121}$ to $R^{151}$ are each independently selected from the group consisting of a hydrogen atom, a fluorine atom, a chlorine atom, a bromine atom, an iodine atom, alkyl groups having from 1 to 9 carbons, alkoxy groups having from 1 to 5 carbons, and aryl groups having from 6 to 12 carbons; $R^{161}$ is selected from alkylene groups having from 1 to 9 carbons; a represents an integer from 0 to 20, and b represents an integer from 1 to 500.

The repeat units in Formula (I) may be the same or different.

In Formula (I), $R^1$ is synonymous with $R^1$ in Formula (A), and preferable ranges are also the same. The $R^1$ moieties at the two terminal ends in Formula (I) may be the same or different. From the viewpoint of ease of synthesis, the $R^1$ moieties are preferably the same. Furthermore, an aspect, in which one of the $R^1$ moieties at the two terminal ends is a phenyl group and the other $R^1$ moiety is a hydrogen atom, is also preferred.

In Formula (I), $R^{13}$ to $R^{16}$ are each independently preferably a hydrogen atom, a fluorine atom, a chlorine atom, a bromine atom, an iodine atom, an alkyl group having from 1 to 9 carbons, an alkoxy group having from 1 to 5 carbons, an aryl group having from 6 to 12 carbons, or an aralkyl group having from 7 to 17 carbons, more preferably a hydrogen atom or an alkyl group having from 1 to 9 carbons, and even more preferably a hydrogen atom. Among $R^{13}$ to $R^{16}$, the alkyl group, the alkoxy group, and the aryl group may have a substituent. The substituent that may be contained in these groups is each independently preferably an alkyl group having from 1 to 5 carbons, an alkenyl group having from 2 to 5 carbons, or an alkoxy group having from 1 to 5 carbons, more preferably an alkyl group having from 1 to 5 carbons or an alkenyl group having from 2 to 5 carbons, and even more preferably an alkyl group having from 1 to 5 carbons. $R^{13}$ to $R^{16}$ preferably contain no substituent.

In Formula (I), one repeating unit has two $R^{13}$ moieties that may be the same or different. The same applies to the symbols $R^{14}$ to $R^{16}$ and the like.

In Formula (I), $R^2$ to $R^7$ are synonymous with $R^2$ to $R^7$ in Formula (A), and preferable ranges are also the same.

In Formula (I), n is preferably an integer from 20 to 150.

Among Formulas (I-1), X is preferably the following groups:

[Chemical Formula 16]

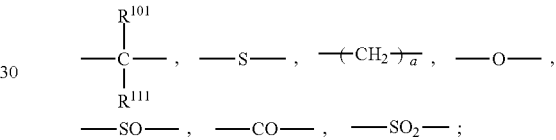

and X is more preferably the following groups.

[Chemical Formula 17]

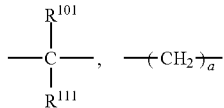

In Formulas (I-1), $R^{101}$ and $R^{111}$ are each independently preferably a hydrogen atom, an alkyl group having from 1 to 9 carbons, or an aryl group having from 6 to 12 carbons, more preferably a hydrogen atom or an alkyl group having from 1 to 9 carbons, even more preferably a hydrogen atom or a methyl group, and yet even more preferably a methyl group. In the case where $R^{101}$ and $R^{111}$ are each an alkyl group or an aryl group, $R^{101}$ and $R^{111}$ may each have a substituent. The substituent is preferably a hydrogen atom, a fluorine atom, a chlorine atom, a bromine atom, an iodine atom, an alkyl group having from 1 to 9 carbons, an alkoxy group having from 1 to 5 carbons, an aryl group having from 6 to 12 carbons, and an aralkyl group having from 7 to 17 carbons, more preferably a hydrogen atom, an alkyl group having from 1 to 9 carbons, or an aryl group having from 6 to 12 carbons, and even more preferably a hydrogen atom or an alkyl group having from 1 to 9 carbons. $R^{101}$ and $R^{111}$ preferably contain no substituent.

In Formulas (I-1), $R^{121}$ and $R^{131}$ are each independently preferably a hydrogen atom, an alkyl group having from 1 to 9 carbons, or an aryl group having from 6 to 12 carbons, and more preferably a hydrogen atom or an alkyl group having from 1 to 9 carbons. In the case where $R^{121}$ and $R^{131}$ are each an alkyl group, an alkoxy group, or an aryl group, $R^{121}$ and $R^{131}$ may contain a substituent. The substituent that may be contained in these groups is preferably an alkyl group having from 1 to 5 carbons, an alkoxy group having from 1 to 5 carbons, a fluorine atom, a chlorine atom, a bromine atom, or an iodine atom, more preferably an alkyl group having from 1 to 5 carbons or an alkoxy group having from 1 to 5 carbons, and even more preferably an alkyl group having from 1 to 5 carbons. $R^{121}$ and $R^{131}$ preferably contain no substituent.

In Formulas (I-1), $R^{141}$ and $R^{151}$ are each independently preferably a hydrogen atom, an alkyl group having from 1 to 9 carbons, or an aryl group having from 6 to 12 carbons, and more preferably a hydrogen atom or an alkyl group having from 1 to 9 carbons. In the case where $R^{141}$ and $R^{151}$ are each an alkyl group, alkoxy group, or an aryl group, $R^{141}$ and $R^{151}$ may contain a substituent. The substituent that may be contained in these groups is an alkyl group having from 1 to 5 carbons, an alkoxy group having from 1 to 5 carbons, a fluorine atom, a chlorine atom, a bromine atom, or an iodine atom, preferably an alkyl group having from 1 to 5 carbons or an alkoxy group having from 1 to 5 carbons, and more preferably an alkyl group having from 1 to 5 carbons. $R^{141}$ and $R^{151}$ preferably contain no substituent.

In Formulas (I-1), $R^{161}$ is preferably an alkylene group having from 1 to 5 carbons, and more preferably an ethylene group or a propylene group. In the case where $R^{161}$ is an alkyl group, an alkoxy group, or an aryl group, $R^{161}$ may contain a substituent. The substituent that may be contained in these groups is preferably an alkyl group having from 1 to 5 carbons, an alkoxy group having from 1 to 5 carbons, a fluorine atom, a chlorine atom, a bromine atom, or an iodine atom, more preferably an alkyl group having from 1 to 5 carbons or an alkoxy group having from 1 to 5 carbons, and even more preferably an alkyl group having from 1 to 5 carbons.

In Formulas (I-1), a is preferably an integer from 0 to 1.

In Formulas (I-1), b is preferably an integer from 1 to 200, and more preferably an integer from 10 to 200.

The polycarbonate resin represented by Formula (I) is preferably a polycarbonate resin represented by Formula (II).

X in Formula (II) is synonymous with X in Formula (I), and preferable ranges are also the same.

The viscosity average molecular weight of the polycarbonate resin used in an embodiment of the present invention is from $1 \times 10^4$ to $5 \times 10^4$, preferably from $1.2 \times 10^4$ to $3 \times 10^4$, and more preferably from $1.8 \times 10^4$ to $2.7 \times 10^4$. Within such a range, good balance between excellent fluidity during molding and mechanical strength can be maintained more effectively.

The viscosity average molecular weight (Mv) is determined by subjecting a solution of the polycarbonate resin in dichloromethane at a concentration of 0.2 g/dL to measurement using a Ubbelohde capillary viscometer at a temperature of 20° C., determining the intrinsic viscosity [η] (dL/g) by using a Huggins coefficient of 0.45, and performing calculation based on the following equation.

$$\eta = 1.23 \times 10^{-4} \times Mv^{0.83} \qquad \text{[Equation 1]}$$

The polycarbonate resin used in an embodiment of the present invention can be synthesized by a publicly known method, and examples of the method include various synthesis methods, such as interfacial polymerization method, pyridine method, transesterification method, and ring-opening polymerization method of cyclic carbonate compound. Specifically, the polycarbonate resin is a polymer or copolymer of aromatic polycarbonate that may be linear or branched and that is obtained by reacting a dihydroxy compound (typically, aromatic dihydroxy compound) or the dihydroxy compound and a small amount of polyhydroxy compound, with a carbonyl chloride, known generally as phosgene, or a carbonyl-based compound such as carbon monoxide, carbon dioxide, and carbonate diester, which is representatively exemplified by dimethyl carbonate and diphenyl carbonate. The terminal structure of the polycarbonate resin used in an embodiment of the present invention can be formed by using a particular end-capping agent.

Specific examples thereof include end-capping agents for polycarbonate resins represented by Formula (1) below.

[Chemical Formula 18]

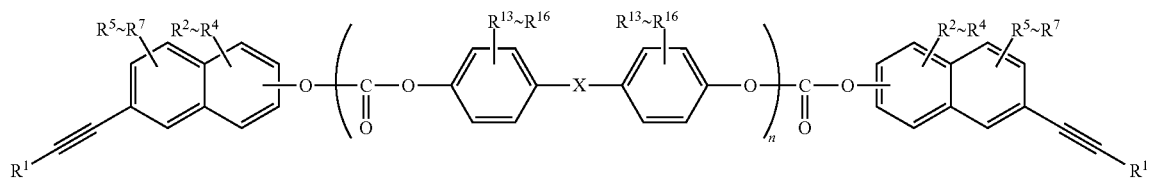

Formula (II)

$R^1$ in Formula (II) is synonymous with $R^1$ in Formula (I), and preferable ranges are also the same. In particular, $R^1$ is preferably a hydrogen atom or an unsubstituted phenyl group.

$R^2$ to $R^7$ in Formula (II) are each independently synonymous with $R^2$ to $R^7$ in Formula (I), and preferable ranges are also the same.

$R^{13}$ to $R^{16}$ in Formula (II) are each independently synonymous with $R^{13}$ to $R^{16}$ in Formula (I), and preferable ranges are also the same.

n in Formula (II) is synonymous with n in Formula (I), and preferable ranges are also the same.

[Chemical Formula 19]

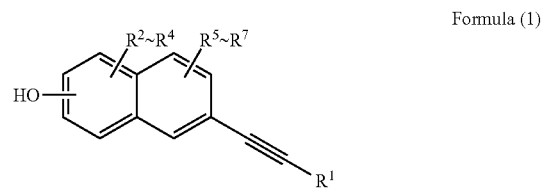

Formula (1)

In Formula (1), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

Formula (1) is preferably represented by Formula (2) below.

[Chemical Formula 20]

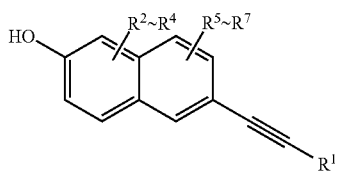

Formula (2)

In Formula (2), $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

Formula (1) is more preferably represented by Formula (3) below.

[Chemical Formula 21]

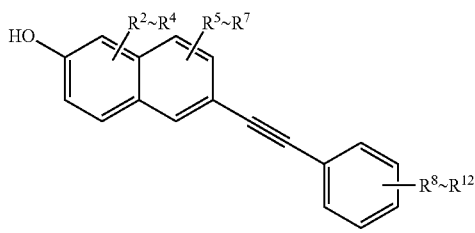

Formula (3)

In Formula (3), $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

$R^1$ to $R^{12}$ in Formulas (1) to (3) are each independently synonymous with $R^1$ to $R^{12}$ in Formulas (A) to (C), and preferable ranges are also the same.

Specific examples of Formulas (1) to (3) include 6-(3,5-dimethoxyphenyl)ethynyl-2-naphthol and the like in addition to the compounds described in Examples below.

Examples of the aromatic dihydroxy compound as the raw material of the polycarbonate resin in an embodiment of the present invention include 2,2-bis(4-hydroxyphenyl)propane [=bisphenol A], bis(4-hydroxyphenyl)-p-diisopropylbenzene, 4,4'-dihydroxydiphenyl, 2,2-bis(4-hydroxy-3,5-dimethylphenyl)propane, 2,2-bis(4-hydroxy-3-methylphenyl) propane, 2,2-bis(4-hydroxy-3,5-diethylphenyl)propane, 2,2-bis(4-hydroxy-3,5-diphenylphenyl)propane, 2,2-bis(4-hydroxy-3,5-dibromophenyl)propane, 2,2-bis(4-hydroxyphenyl)pentane, 2,4'-dihydroxy-diphenylmethane, bis-(4-hydroxyphenyl)methane, bis-(4-hydroxy-3-nitrophenyl)methane, 1,1-bis(4-hydroxyphenyl)ethane, 3,3-bis(4-hydroxyphenyl)pentane, 1,1-bis(4-hydroxyphenyl)cyclohexane [=bisphenol Z], bis(4-hydroxyphenyl)sulfone, 2,4'-dihydroxydiphenylsulfone, bis(4-hydroxyphenyl)sulfide, 4,4'-dihydroxydiphenylether, 4,4'-dihydroxy-3,3'-dimethyldiphenylether, 4,4'-dihydroxy-2,5-diethoxydiphenylether, 1-phenyl-1,1-bis(4-hydroxyphenyl)ethane, 1,1-bis(4-hydroxy-3-methylphenyl)cyclohexane, 1-phenyl-1,1-bis(4-hydroxy-3-methylphenyl)ethane, bis(4-hydroxyphenyl)diphenylmethane, 9,9-bis(4-hydroxyphenyl)fluorene, 9,9-bis(4-hydroxy-3-methylphenyl)fluorene, and 2,2-bis(4-hydroxyphenyl)hexafluoropropane. Bis(4-hydroxyphenyl) alkanes are preferred, and 2,2-bis(4-hydroxyphenyl)propane [bisphenol A] and 1,1-bis(4-hydroxyphenyl)cyclohexane [bisphenol Z] are particularly preferred.

One type of these aromatic dihydroxy compounds can be used, or a mixture of two or more types of these aromatic dihydroxy compounds can be used. Furthermore, as a part of the dihydroxy compounds, a compound in which at least one tetraalkylphosphonium sulfonate is bonded to the aromatic dihydroxy compound described above, a polymer or oligomer having a siloxane structure and containing phenolic OH groups at the both terminal ends, and the like may be used together.

To obtain a branched polycarbonate resin, a polyhydroxy compound, such as phloroglucin, 4,6-dimethyl-2,4,6-tris(4-hydroxyphenyl)heptene-2,4,6-dimethyl-2,4,6-tris(4-hydroxyphenyl)heptane, 2,6-dimethyl-2,4,6-tris(4-hydroxyphenyl)heptene-3,1,3,5-tris(4-hydroxyphenyl)benzene, or 1,1,1-tris(4-hydroxyphenyl)ethane; or 3,3-bis(4-hydroxyaryl)oxyindole (=isatin bisphenol), 5-chloroisatin bisphenol, 5,7-dichloroisatin bisphenol, 5-bromoisatin bisphenol, or the like needs to be used as a part of the aromatic dihydroxy compounds described above. The used amount thereof is preferably from 0.01 to 10 mol %, and more preferably from 0.1 to 3 mol %, relative to the amount of the aromatic dihydroxy compound.

In the reaction by interfacial polymerization method, a polycarbonate resin can be obtained by, in the presence of an organic solvent which is inert against the reaction and an aqueous alkali solution while pH is typically maintained to 10 or higher, preparing an aromatic dihydroxy compound and an end-capping agent, and as necessary an antioxidant for prevention of oxidation of the aromatic dihydroxy compound, and carrying out the reaction with phosgene, followed by adding a polymerization catalyst, such as a tertiary amine or a quaternary ammonium salt, to perform interfacial polymerization. The moment for the addition of the end-capping agent is not particularly limited as long as it is between the phosgenation and the start of the polymerization reaction. Note that the reaction temperature is from 0 to 35° C., and the reaction time is from a few minutes to several hours.

Here, examples of the organic solvent which is inert against the reaction include chlorinated hydrocarbons, such as dichloromethane, 1,2-dichloroethane, chloroform, monochlorobenzene, and dichlorobenzene; and aromatic hydrocarbons, such as benzene, toluene, and xylene. As the end-capping agent, in addition to the compound having a triple bond described above, a compound having a monovalent phenolic hydroxy group can be used together provided that it does not impair the effect of the present invention, and specific examples thereof include m-methylphenol, p-methylphenol, m-propylphenol, p-propylphenol, p-tert-butylphenol, and p-long chain alkyl-substituted phenol. Examples of the polymerization catalyst include tertiary amines, such as trimethylamine, triethylamine, tributylamine, tripropylamine, trihexylamine, and pyridine; and quaternary ammonium salts, such as trimethylbenzylammonium chloride, tetramethylammonium chloride, and triethylbenzylammonium chloride.

The reaction by transesterification method is a transesterification reaction of a diester carbonate and an aromatic dihydroxy compound. Typically, the desired molecular weight and terminal hydroxyl group amount of the polycarbonate resin can be determined by adjusting, for example, the mixing ratio of the diester carbonate and the aromatic dihydroxy compound and the degree of pressure reduction during the reaction. The amount of the terminal hydroxyl group remarkably affects the thermal stability, hydrolytic stability, hue, and the like of the polycarbonate resin, and to impart practical physical properties, the amount of the terminal hydroxyl group is preferably 1000 ppm by mass or less and more preferably 700 ppm by mass or less. The lower limit is preferably 100 ppm by mass or greater. In the transesterification reaction, typically, not less than the equimolar amount, and preferably from 1.01 to 1.30 mol, of the diester carbonate is used per 1 mol of the aromatic dihydroxy compound.

Examples of the diester carbonate include dialkyl carbonate compounds, such as dimethyl carbonate, diethyl carbonate, and di-tert-butyl carbonate; and diphenyl carbonate and substituted diphenyl carbonates, such as di-p-tolyl carbonate, phenyl-p-tolyl carbonate, and di-p-chlorophenyl carbonate. Among these, diphenyl carbonate and substituted diphenyl carbonates are preferred, and diphenyl carbonate is particularly preferred.

One type of these diester carbonate compounds can be used, or a mixture of two or more types of these diester carbonate compounds can be used.

When the polycarbonate resin is synthesized by the transesterification method, typically, a transesterification catalyst is used. The transesterification catalyst is not particularly limited, but mainly an alkali metal compound and/or an alkaline earth metal compound is used, and a basic compound, such as a basic boron compound, a basic phosphorus compound, a basic ammonium compound, or an amine-based compound, can be supplementally used together with the alkali metal compound and/or the alkaline earth metal compound. An example of the transesterification reaction that uses such raw materials is a method, in which the reaction is performed at a temperature of 100 to 320° C. and finally a melt polycondensation reaction is performed under reduced pressure at or below $2.7 \times 10^2$ Pa (2 mmHg) while by-products such as aromatic hydroxy compounds are removed. The melt polycondensation can be performed continuously or in batches; however, for the polycarbonate resin used in the present invention, the melt polycondensation is preferably performed continuously from the viewpoint of stability and the like. In the transesterification method, as the deactivating agent of the catalyst in the polycarbonate resin, use of a compound that neutralizes the catalyst, such as sulfur-containing acidic compound, or a derivative formed therefrom is preferred. The used amount thereof is preferably from 0.5 to 10 equivalents and more preferably from 1 to 5 equivalents, based on the amount of the alkali metal as the catalyst, and is typically from 1 to 100 ppm by mass and preferably from 1 to 20 ppm by mass, based on the amount of the polycarbonate resin.

The polycarbonate resin obtained by the method described above is prepared into a polycarbonate resin composition. Flake of the polycarbonate resin composition can be obtained, for example, by adding a methylene chloride solution containing the polycarbonate resin obtained by interfacial polymerization method into warm water kept at 45° C. dropwise and then removing the solvent by evaporation; or by adding a methylene chloride solution containing the polycarbonate resin obtained by interfacial polymerization method into methanol, then collecting the precipitated polymer by filtration and drying; or by agitating and pulverizing the polycarbonate resin obtained by interfacial polymerization method through agitating a methylene chloride solution containing the polycarbonate resin in a kneader while the temperature is maintained at 40° C., and then removing the solvent using hot water at or above 95° C.

As necessary, after the polycarbonate resin is isolated by a publicly known method, polycarbonate resin composition pellets can be obtained by, for example, a cold cut method based on a known strand process (a method in which the polycarbonate resin composition that has been once melted is formed into strands, cooled, cut into a predetermined shape, and pelletized), a hot cut method based on an in-air hot cut process (method in which the polycarbonate resin composition that has been once melted is cut into pellets in the air before being brought into contact with water), or a hot cut method based on an underwater hot cut process (the polycarbonate resin composition that has been once melted is cut under water and cooled at the same time to produce pellets). Note that the obtained polycarbonate resin composition pellets are, as necessary, preferably dried by a drying method using a hot air dryer, a vacuum dryer, or a dehumidification dryer.

The polycarbonate resin composition according to an embodiment of the present invention preferably contains from 40 to 99.99 mass %, more preferably from 60 to 99.99 mass %, and even more preferably 70 to 99.9 mass %, of the polycarbonate resin according to an embodiment of the present invention having a terminal structure represented by Formula (A) above and having the viscosity average molecular weight of $1 \times 10^4$ to $5 \times 10^4$.

The polycarbonate resin composition according to an embodiment of the present invention may contain one type or two or more types of the polycarbonate resins according to an embodiment of the present invention. In a case where two or more types thereof are contained therein, the total amount is preferably within the range described above.

As necessary, the polycarbonate resin composition according to an embodiment of the present invention may contain a resin other than the polycarbonate resin according to an embodiment of the present invention as long as the desired physical properties are not remarkably impaired. Examples of such other resin include thermoplastic polyester resins, such as polycarbonate resins other than the polycarbonate resin according to an embodiment of the present invention, polyethylene terephthalate resins (PET resins), polytrimethylene terephthalate resins (PTT resins), and polybutylene terephthalate resins (PBT resins); styrene-based resins, such as polystyrene resins (PS resins), high-impact polystyrene resins (HIPS), acrylonitrile-styrene copolymers (AS resins), and methyl methacrylate-styrene copolymers (MS resins); core/shell type elastomers, such as methyl methacrylate-acrylic rubber-styrene copolymers (MAS), and elastomers such as polyester-based elastomers; polyolefin resins, such as cyclic cycloolefin resins (COP resins) and cyclic cycloolefin (COP) copolymer resins; polyamide resins (PA resins); polyimide resins (PI resins); polyetherimide resins (PEI resins); polyurethane resins (PU resins); polyphenylene ether resins (PPE resins); polyphenylene sulfide resins (PPS resins); polysulfone resins (PSU resins); polymethacrylate resins (PMMA resins); and polycaprolactone.

In the polycarbonate resin composition of the present invention, the blended proportion of the resin components other than the polycarbonate resin is preferably 10 mass % or less of the amount of the all resin components, and preferably, substantially no other resin component other than the polycarbonate resin is contained. "Substantially no . . . is contained" means, for example, not actively blending as a resin component. An example is 1 mass % or less of the all resin components. The polycarbonate resin composition of the present invention may contain one type or two or more types of resin components other than the polycarbonate resin. In a case where two or more types thereof are contained therein, the total amount is preferably within the range described above.

Stabilizer

The polycarbonate resin composition of the present invention contains a stabilizer. Examples of the stabilizer include thermal stabilizers and antioxidants. In the case where the stabilizer is blended, the added proportion of the stabilizer is preferably 0.001 parts by mass or greater, more preferably 0.01 parts by mass or greater, even more preferably 0.02 parts by mass or greater, but preferably 2 parts by mass or less, more preferably 1.4 parts by mass or less, and even more preferably 1.0 part by mass or less, per 100 parts by mass of the polycarbonate resin. Only one type of the stabilizers may be contained, or two or more types of the stabilizers may be contained. In a case where two or more types thereof are contained therein, the total amount is preferably within the range described above.

Thermal Stabilizer

Examples of the thermal stabilizer include phenol-based, phosphorus-based, and sulfur-based thermal stabilizers. Specific examples thereof include oxoacids of phosphorus, such as phosphoric acid, phosphonic acid, phosphorous acid, phosphinic acid, and polyphosphoric acid; metal acid pyrophosphates, such as sodium acid pyrophosphate, potassium acid pyrophosphate, and calcium acid pyrophosphate; phosphates of group I metal or group X metal, such as potassium phosphate, sodium phosphate, cesium phosphate, and zinc phosphate; organophosphate compounds, organophosphite compounds, and organophosphonite compounds. Examples also include at least one type selected from the group consisting of phosphite compounds (a) in which at least one ester in the molecule is subjected to esterification by phenol and/or phenol containing at least one alkyl group having from 1 to 25 carbons, phosphorous acid (b), and tetrakis(2,4-di-tert-butylphenyl)-4,4'-biphenylene-di-phosphonite (c). Specific examples of the phosphite compound (a) include trioctyl phosphite, trioctadecyl phosphite, tridecyl phosphite, trilauryl phosphite, tristearyl phosphite, triphenyl phosphite, tris(monononylphenyl)phosphite, tris(monononyl/dinonylphenyl)phosphite, trisnonylphenyl phosphite, tris(octylphenyl)phosphite, tris(2,4-di-tert-butylphenyl) phosphite, trinonylphosphite, didecylmonophenyl phosphite, dioctylmonophenyl phosphite, diisopropylmonophenyl phosphite, monobutyldiphenyl phosphite, monodecyldiphenyl phosphite, bis(2,4-di-tert-butylphenyl) pentaerythritol phosphite, bis(2,6-di-tert-butyl-4-methylphenyl)pentaerythritol phosphite, monooctyldiphenyl phosphite, distearylpentaerythritol diphosphite, tricyclohexyl phosphite, diphenylpentaerythritol diphosphite, bis(2,6-di-tert-butyl-4-methylphenyl)pentaerythritol diphosphite, 2,2-methylenebis(4,6-di-tert-butylphenyl)octyl phosphite, bis(nonylphenyl)pentaerythritol diphosphite, bis(2,4-di-tert-butylphenyl)pentaerythritol diphosphite, and bis(2,6-di-tert-butyl-4-ethylphenyl)pentaerythritol diphosphite. One type of these may be used alone, or a mixture of two or more types of these may be used.

Examples of the organophosphite compound include ADK STAB 1178 (trade name; hereinafter the same), ADK STAB 2112, and ADK STAB HP-10, available from Adeka Corporation; JP-351, JP-360, and JP-3CP, available from Johoku Chemical Co., Ltd.; and Irgafos 168, available from BASF.

Furthermore, examples of the phosphate include trimethyl phosphate, triethyl phosphate, tributyl phosphate, trioctyl phosphate, triphenyl phosphate, tricresyl phosphate, tris(nonylphenyl)phosphate, and 2-ethylphenyldiphenyl phosphate.

In the case where the thermal stabilizer is blended, the added proportion of the thermal stabilizer is preferably 0.001 parts by mass or greater, more preferably 0.01 parts by mass or greater, even more preferably 0.03 parts by mass or greater, but preferably 1 part by mass or less, more preferably 0.7 parts by mass or less, and even more preferably 0.5 parts by mass or less, per 100 parts by mass of the polycarbonate resin.

Only one type of the thermal stabilizers may be contained, or two or more types of the thermal stabilizers may be contained. In a case where two or more types thereof are contained therein, the total amount is preferably within the range described above.

Antioxidant

Examples of the antioxidant include phenol-based antioxidants, hindered phenol-based antioxidants, bisphenol-based antioxidants, and polyphenol-based antioxidants. Specific examples thereof include 2,6-di-tert-butyl-4-methylphenol, tris(3,5-di-tert-butyl-4-hydroxybenzyl) isocyanurate, n-octadecyl-3-(3',5'-di-tert-butyl-4'-hydroxyphenyl)propionate, tetrakis[methylene-3-(3,5-di-tert-butyl-4-hydroxyphenyl)propionate]methane, 4,4'-butylidene bis(3-methyl-6-tert-butylphenol), triethylene glycol bis[3-(3-tert-butyl-4-hydroxy-5-methylphenyl)propionate], 3,9-bis{2-[3-(3-tert-butyl-4-hydroxy-5-methylphenyl)propionyloxy]-1,1-dimethylethyl}-2,4,8,10-tetraoxaspiro[5,5]undecane, pentaerythritol tetrakis[3-(3,5-di-tert-butyl-4-hydroxyphenyl)propionate], thiodiethylene bis[3-(3,5-di-tert-butyl-4-hydroxyphenyl)propionate], N,N'-hexane-1,6-diyl bis[3-(3,5-di-tert-butyl-4-hydroxyphenylpropionamide)], 2,4-dimethyl-6-(1-methylpentadecyl)phenol, diethyl[[3,5-bis(1,1-dimethylethyl)-4-hydroxyphenyl]methyl]phosphate, 3,3',3",5,5',5"-hexa-tert-butyl-a,a',a"-(mesitylene-2,4,6-triyl)tri-p-cresol, 4,6-bis(octylthiomethyl)-o-cresol, ethylene bis(oxyethylene)bis[3-(5-tert-butyl-4-hydroxy-m-tolyl) propionate], hexamethylene bis[3-(3,5-di-tert-butyl-4-hydroxyphenyl)propionate], 1,3,5-tris(3,5-di-tert-butyl-4-hydroxybenzyl)-1,3,5-triazine-2,4,6(1H,3H,5H)-trione, and 2,6-di-tert-butyl-4-(4,6-bis(octylthio)-1,3,5-triazin-2-ylamino)phenol.

Examples of the phenol-based antioxidant include Irganox 1010 (trade name; hereinafter the same) and Irganox 1076, available from BASF; and ADK STAB AO-50 and ADK STAB AO-60, available from Adeka Corporation.

In the case where the antioxidant is blended, the added proportion of the antioxidant is preferably 0.001 parts by mass or greater, and more preferably 0.01 parts by mass or greater, but preferably 1 part by mass or less and more preferably 0.5 parts by mass or less, per 100 parts by mass of the polycarbonate resin.

Only one type of the antioxidant may be contained, or two or more types of the antioxidants may be contained. In a case where two or more types thereof are contained therein, the total amount is preferably within the range described above.

The polycarbonate resin composition of the present invention may contain various types of additives unless the scope of the present invention is departed. Examples of the additive include at least one type of additive selected from the group consisting of flame retardants, flame retardant auxiliaries, ultraviolet absorbing agents, mold release agents, and coloring agents. At least one type of flame retardants or mold release agents is preferably contained.

Furthermore, an antistatic agent, a fluorescent brightener, an antifogging agent, a fluidity modifier, a plasticizer, a dispersant, an antibacterial agent, or the like may be added as long as the desired physical properties are not significantly impaired.

Flame Retardant

The polycarbonate resin composition according to an embodiment of the present invention may contain, as a flame retardant, an organometallic salt-based flame retardant, a phosphorus-based flame retardant, a silicone-based flame retardant, or the like. Examples of the flame retardant that can be used in an embodiment of the present invention include flame retardants (flame retardant compositions) described in paragraphs 0085 to 0093 of JP 2016-183422 A, and the disclosure is incorporated herein by reference.

In the case where the flame retardant is contained, the polycarbonate resin composition according to an embodiment of the present invention preferably contains a metal salt of an organic sulfonic acid.

Examples of the metal salt of an organic sulfonic acid include metal salts of aliphatic sulfonic acids and metal salts of aromatic sulfonic acids. One type of these may be used alone, or two or more types of these may be used in combination. As the metal salt, alkali metal salts and alkaline earth metal salts are preferred.

Examples of the alkali metal include sodium, lithium, potassium, rubidium, and cesium. Examples of the alkaline earth metal include calcium and strontium. The preferred metal of the metal salt of the organic sulfonic acid used in an embodiment of the present invention is an alkali metal, such as sodium, potassium, rubidium, cesium, and more preferably sodium or potassium. Employing such a metal can promote a carbonized layer formation during combustion effectively, and achieve the effect of maintaining high transparency.

Examples of the aliphatic sulfonate preferably include metal salts of fluoroalkane-sulfonic acids, and more preferably metal salts of perfluoroalkane-sulfonic acids.

Examples of the metal salt of the fluoroalkane-sulfonic acid include alkali metal salts and alkaline earth metal salts, and alkali metal salts are preferred.

The number of carbons of the metal salt of the fluoroalkane-sulfonic acid is preferably from 1 to 8, and more preferably from 2 to 4. The metal salt of the fluoroalkane-sulfonic acid having carbons in such a range can achieve the effect of maintaining high transparency.

Preferable specific examples of the metal salt of the fluoroalkane-sulfonic acid include sodium perfluorobutane sulfonate, potassium perfluorobutane sulfonate, sodium perfluoroethane sulfonate, and potassium perfluoroethane sulfonate.

Examples of the metal salt of the aromatic sulfonic acid include alkali metal salts and alkaline earth metal salts, and alkali metal salts are preferred.

Specific examples of the alkali metal salt of the aromatic sulfonic acid include sodium 3,4-dichlorobenzene sulfonate, sodium 2,4,5-trichlorobenzene sulfonate, sodium benzene sulfonate, sodium salt of diphenylsulfone-3-sulfonic acid, potassium salt of diphenylsulfone-3-sulfonic acid, sodium salt of 4,4'-dibromodiphenyl-sulfone-3-sulfonic acid, potassium salt of 4,4'-dibromophenyl-sulfone-3-sulfonic acid, disodium salt of diphenylsulfone-3,3'-disulfonic acid, dipotassium salt of diphenylsulfone-3,3'-disulfonic acid, sodium dodecylbenzene sulfonate, potassium dodecylbenzene sulfonate, potassium p-toluene sulfonate, and potassium p-styrene sulfonate.

In particular, from the viewpoint of enhancing transparency, the metal salt of the organic sulfonic acid used in an embodiment of the present invention is preferably potassium salt of diphenylsulfone-3-sulfonic acid, potassium p-toluene sulfonate, potassium p-styrene sulfonate, or potassium dodecylbenzene sulfonate, and is more preferably potassium salt of diphenylsulfone-3-sulfonic acid.

Note that, in the case where the flame retardant is blended, the added mass of the flame retardant is preferably from 0.005 parts by mass to 0.2 parts by mass, more preferably from 0.01 parts by mass to 0.15 parts by mass, and even more preferably from 0.03 parts by mass to 0.12 parts by mass, per 100 parts by mass of the polycarbonate resin.

The polycarbonate resin composition according to an embodiment of the present invention can be substantially free of a flame retardant. "Substantially free of" means that the blended amount of the flame retardant is less than 0.005 parts by mass per 100 parts by mass of the polycarbonate resin.

Furthermore, in the case where the flame retardant is contained in the polycarbonate resin composition according to an embodiment of the present invention, an embodiment in which the compounded amount of another flame retardant other than the metal salt of the organic sulfonic acid is 0.1 mass % or less of the content of the metal salt of the organic sulfonic acid is exemplified.

Flame Retardant Auxiliary

For example, a silicone compound can be added as a flame retardant auxiliary. The silicone compound preferably has a phenyl group in the molecule. Having a phenyl group, the silicone compound exhibits improved dispersibility in the polycarbonate resin, and achieves excellent transparency and flame retardancy. The weight average molecular weight of the silicone compound is preferably from 450 to 5000, more preferably from 750 to 4000, even more preferably from 1000 to 3000, and particularly preferably from 1500 to 2500. The weight average molecular weight of 450 or greater can facilitate easier production and easier adaptation to industrial production, and readily enhance heat resistance of the silicone compound. On the other hand, when the silicone compound has the weight average molecular weight of 5000 or less, decrease of its dispersibility in the polycarbonate resin composition tends to be effectively suppressed, and deterioration of flame retardancy of the polycarbonate resin composition and deterioration of mechanical properties tend to be more effectively suppressed.

In the case where the flame retardant auxiliary is blended, the added proportion of the flame retardant auxiliary is preferably 0.1 parts by mass or greater, and more preferably 0.2 parts by mass or greater, but preferably 7.5 parts by mass or less, and more preferably 5 parts by mass or less, per 100 parts by mass of the polycarbonate resin. When the added proportion of the flame retardant auxiliary is not less than the lower limit, flame retardancy is effectively exhibited. When the added proportion of the flame retardant auxiliary is not greater than the upper limit, appearance defects such as delamination can be effectively suppressed. One type of flame retardant auxiliaries may be used, or two or more types of flame retardant auxiliaries may be used. When two or more types are used, the total amount is preferably within the range described above.

Ultraviolet Absorbing Agent

Besides inorganic ultraviolet absorbing agents such as cerium oxide and zinc oxide, examples of the ultraviolet absorbing agent include organic ultraviolet absorbing agents, such as benzotriazole compounds, benzophenone compounds, salicylate compounds, cyanoacrylate compounds, triazine compounds, oxanilide compounds, malonate compounds, hindered amine compounds, and phenyl salicylate compounds. Among these, benzotriazole-based and benzophenone-based organic ultraviolet absorbing agents are preferred. In particular, specific examples of the benzotriazole compound include 2-(2'-hydroxy-5'-methylphenyl)benzotriazole, 2-[2'-hydroxy-3',5'-bis(α,α-dimethylbenzyl)phenyl]-benzotriazole, 2-(2'-hydroxy-3',5'-di-tert-butyl-phenyl)-benzotriazole, 2-(2'-hydroxy-3'-tert-butyl-5'-methylphenyl)-5-chlorobenzotriazole, 2-(2'-hydroxy-3',5'-di-tert-butyl-phenyl)-5-chlorobenzotriazole, 2-(2'-hydroxy-3',5'-di-tert-amyl)-benzotriazole, 2-(2'-hydroxy-5'-tert-octylphenyl)benzotriazole, 2,2'-methylene bis[4-(1,1,3,3-tetramethylbutyl)-6-(2N-benzotriazol-2-yl)phenol], 2-(4,6-diphenyl-1,3,5-triazin-2-yl)-5-[(hexyl)oxy]-phenol, 2-[4,6-bis(2,4-dimethylphenyl)-1,3,5-triazin-2-yl]-5-(octyloxy) phenol, 2,2'-(1,4-phenylene)bis[4H-3,1-benzoxazin-4-one], [(4-methoxyphenyl)-methylene]-propanedioic acid-dim-ethyl ester, 2-(2H-benzotriazol-2-yl)-p-cresol, 2-(2H-benzotriazol-2-yl)-4,6-bis(1-methyl-1-phenylmethyl)phenol, 2-[5-chloro(2H)-benzotriazol-2-yl]-4-methyl-6-(tert- butyl) phenol, 2,4-di-tert-butyl-6-(5-chlorobenzotriazol-2-yl)phenol, 2-(2H-benzotriazol-2-yl)-4-(1,1,3,3-tetrabutyl)phenol, 2,2'-methylene bis[6-(2H-benzotriazol-2-yl)-4-(1,1,3,3-tetrabutyl)phenol], and [methyl-3-[3-tert-butyl-5-(2H-benzotriazol-2-yl)-4-hydroxyphenyl]propionate-polyethylene glycol] condensates. Among those described above, 2-(2'-hydroxy-5'-tert-octylphenyl)benzotriazole, 2,2'-methylene bis[4-(1,1,3,3-tetramethylbutyl)-6-(2N-benzotriazol-2-yl) phenol] is preferred. Furthermore, specific examples of the benzophenone-based ultraviolet absorbing agent include 2,4-dihydroxybenzophenone, 2-hydroxy-4-methoxybenzophenone, 2-hydroxy-4-n-octoxybenzophenone, 2-hydroxy-4-dodecyloxybenzophenone, 2-hydroxy-4-octadecyloxybenzophenone, 2,2'-dihydroxy-4-methoxybenzophenone, 2,2'-dihydroxy-4,4'-dimethoxybenzophenone, and 2,2',4,4'-tetrahydroxybenzophenone. Furthermore, specific examples of the phenyl salicylate-based ultraviolet absorbing agent include phenylsalicylate, and 4-tert-butyl-phenylsalicylate. Furthermore, specific examples of the triazine-based ultraviolet absorbing agent include 2-(4,6-diphenyl-1,3,5-triazin-2-yl)-5-[(hexyl)oxy]-phenol, and 2-[4,6-bis(2,4-dimethylphenyl)-1,3,5-triazin-2-yl]-5-(octyloxy)phenol.

Furthermore, specific examples of the hindered amine-based ultraviolet absorbing agent include bis(2,2,6,6-tetramethylpiperidin-4-yl)sebacate.

In the case where the ultraviolet absorbing agent is blended, the added proportion of the ultraviolet absorbing agent is preferably 0.01 parts by mass or greater and more preferably 0.1 parts by mass or greater, but preferably 3 parts by mass or less and more preferably 1 part by mass or less, per 100 parts by mass of the polycarbonate resin. When the added proportion of the ultraviolet absorbing agent is not less than the lower limit, effect of enhancing weather resistance is effectively exhibited. When the added proportion of the ultraviolet absorbing agent is not greater than the upper limit, mold deposit and the like can be effectively suppressed, and mold contamination can be effectively suppressed.

One type of ultraviolet absorbing agents may be used, or two or more types of ultraviolet absorbing agents may be used. When two or more types are used, the total amount is preferably within the range described above.

Mold Release Agent

Examples of the mold release agent include carboxylate, polysiloxane compounds, and paraffin wax (polyolefin-based). Specific examples thereof include at least one type of compound selected from the group consisting of aliphatic carboxylic acids, esters of aliphatic carboxylic acids and alcohols, aliphatic hydrocarbon compounds having a number average molecular weight from 200 to 15000, and polysiloxane-based silicone oils. Examples of the aliphatic carboxylic acid include saturated or unsaturated aliphatic monovalent, divalent, or trivalent carboxylic acids. Note that aliphatic carboxylic acids also include alicyclic carboxylic acids. Among these, preferred aliphatic carboxylic acids are monovalent or divalent carboxylic acids having from 6 to 36 carbons, and aliphatic saturated monovalent carboxylic acids having from 6 to 36 carbons are even more preferred. Specific examples of the aliphatic carboxylic acid include palmitic acid, stearic acid, valeric acid, caproic acid, capric acid, lauric acid, arachidic acid, behenic acid, lignoceric acid, cerotic acid, melissic acid, tetratriacontanoic acid, montanic acid, glutaric acid, adipic acid, and azelaic acid. As the aliphatic carboxylic acid in the ester of aliphatic carboxylic acid and alcohol, those same as the aliphatic carboxylic acids described above can be used. Meanwhile, examples of the alcohol include saturated or unsaturated monohydric or polyhydric alcohols. These alcohols may have a substituent such as a fluorine atom or an aryl group. Among these, saturated monohydric or polyhydric alcohols having 30 or less carbons are preferred, and aliphatic saturated monohydric alcohols or polyhydric alcohols having 30 or less carbons are more preferred. Note that aliphatic series include alicyclic compounds. Specific examples of the alcohol include octanol, decanol, dodecanol, stearyl alcohol, behenyl alcohol, ethylene glycol, diethylene glycol, glycerin, pentaerythritol, 2,2-dihydroxy perfluoropropanol, neopentylene glycol, ditrimethylol propane, and dipentaerythritol. Note that the ester compound described above may contain an aliphatic carboxylic acid and/or alcohol as an impurity and may be a mixture of a plurality of compounds. Specific examples of the ester of an aliphatic carboxylic acid and an alcohol include beeswax (mixture containing myricyl palmitate as a main component), stearyl stearate, behenyl behenate, stearyl behenate, glycerol monopalmitate, glycerol monostearate, glycerol distearate, glycerol tristearate, pentaerythritol monopalmitate, pentaerythritol monostearate, pentaerythritol distearate, pentaerythritol tristearate, and pentaerythritol tetrastearate. Examples of the aliphatic hydrocarbon having a number average molecular weight from 200 to 15000 include liquid paraffin, paraffin wax, micro wax, polyethylene wax, Fischer-Tropsch wax, and α-olefin oligomers having from 3 to 12 carbons. Note that aliphatic hydrocarbons also include alicyclic hydrocarbons. Furthermore, these hydrocarbon compounds may be partially oxidized. Among these, paraffin wax, polyethylene wax, or partial oxides of polyethylene wax are preferred, and paraffin wax and polyethylene wax are more preferred. The number average molecular weight is preferably from 200 to 5000. These aliphatic hydrocarbons may be a single substance or a mixture of substances having various constituents and/or various molecular weights, and the main component needs to be within the ranges described above. Examples of the polysiloxane-based silicone oil include dimethyl silicone oils, phenylmethyl silicone oils, diphenyl silicone oils, and fluorinated alkyl silicones. Two or more types of these may be used in combination.

In the case where the mold release agent is blended, the added proportion of the mold release agent is preferably 0.001 parts by mass or greater and more preferably 0.01 parts by mass or greater, but preferably 2 parts by mass or less and more preferably 1 part by mass or less, per 100 parts by mass of the polycarbonate resin. In the case where the added proportion of the mold release agent is not greater than the lower limit, effect of releasability may be insufficient. In the case where the added proportion of the mold release agent is greater than the upper limit, deterioration of hydrolysis resistance, mold contamination during injection molding, and the like may occur. One type of mold release agent may be used, or two or more types of mold release agents may be used. When two or more types are used, the total amount is preferably within the range described above.

Coloring Agent

The coloring agent may be a dye or a pigment, and examples thereof include inorganic pigments, organic pigments, and organic dyes. Examples of the inorganic pigment include carbon black; sulfide-based pigments, such as cadmium red and cadmium yellow; silicate-based pigments, such as ultramarine blue; oxide-based pigments, such as titanium oxide, zinc oxide, red iron oxide, chromium oxide, iron black, titanium yellow, zinc-iron-based brown, titanium-cobalt-based green, cobalt green, cobalt blue, copper-chromium-based black, and copper-iron-based black; chromate-based pigments, such as chrome yellow and molybdate orange; and ferrocyanide-based pigments, such as Prussian blue. Examples of the organic pigment and organic dye used as a coloring agent include phthalocyanine-based dyes and pigments, such as copper phthalocyanine blue and copper phthalocyanine green; azo-based dyes and pigments, such as nickel azo yellow; condensed polycyclic dyes and pigments, such as thioindigo-based, perinone-based, perylene-based, quinacridone-based, dioxazine-based, isoindolinone-based, and quinophthalone-based condensed polycyclic dyes and pigments; and quinoline-based, anthraquinone-based, heterocyclic, methyl-based pigments and dyes. Among these, titanium oxide, carbon black, cyanine-based, quinoline-based, anthraquinone-based, phthalocyanine-based dyes and pigments, and the like are preferred from the viewpoint of thermal stability.

To enhance the handing properties during extrusion and enhance the dispersibility in the resin composition, the coloring agent may preliminarily be mixed with a polystyrene-based resin, a polycarbonate-based resin, or an acryl-based resin to form a master batch and used.

In the case where the coloring agent is blended, the added proportion of the coloring agent is preferably 5 parts by mass or less, more preferably 3 parts by mass or less, and even more preferably 2 parts by mass or less, but 0.1 parts by mass or greater, per 100 parts by mass of the polycarbonate resin. One type of coloring agent may be used, or two or more types of coloring agents may be used. When two or more types are used, the total amount is preferably within the range described above.

Physical Properties of Polycarbonate Resin Composition

When the polycarbonate resin composition is molded into a test piece having a thickness of 1.0 mm, the polycarbonate resin composition according to an embodiment of the present invention could have a haze of 1.0% or less. The lower limit is preferably 0%; however, the lower limit of 0.4% or greater is still at a practical level. The haze is measured in accordance with the method described below in Examples.

When the polycarbonate resin composition is molded into a test piece having a thickness of 1.0 mm, the polycarbonate resin composition according to an embodiment of the present invention can have a YI (hue) of 10 or less. The lower limit is preferably 0; however, the lower limit of 2 or greater is still at a practical level. The YI is measured in accordance with the method described below in Examples.

The polycarbonate resin composition according to an embodiment of the present invention preferably has a glass transition temperature of 151° C. or higher. The upper limit of the glass transition temperature thereof is not particularly limited; however, for example, the glass transition temperature of 165° C. or lower is sufficiently at a practical level. The glass transition temperature is measured in accordance with the method described below in Examples. If the equipment used is not readily available due to discontinuation of the equipment or the like, another equipment having the equivalent performance can be used.

The polycarbonate resin composition according to an embodiment of the present invention could have a LOI value of 40% or greater and, further, could have a LOI value of 42% or greater. The upper limit is not particularly limited; however, for example, the upper limit of 45% or lower is still at a practical level. The LOI value is measured in accordance with the method described below in Examples.

When formed into a test piece having a thickness of 3.2 mm, the polycarbonate resin composition according to an embodiment of the present invention could have the flame retardancy (UL94 test) of V-0. The flame retardancy (UL94 test) is measured in accordance with the method described below in Examples. In particular, the polycarbonate resin composition according to an embodiment of the present invention is preferably substantially free of a flame retardant and satisfies the flame retardancy described above.

The polycarbonate resin composition according to an embodiment of the present invention preferably satisfies all the values described above for the haze, YI, glass transition temperature, LOT value, and flame retardancy by UL94 test.

Molded Product

The present invention includes the molded article formed from the polycarbonate resin composition.

The molded article according to an embodiment of the present invention is a molded article formed from the polycarbonate resin composition according to an embodiment of the present invention including various preferable embodiments and configurations described above. The shape, pattern, color, dimensions, and the like of the molded article are not limited and can be optionally selected depending on the use thereof. Specific examples of the molded article include electric and electronic equipment, office automation (OA) equipment, information terminal devices, machinery parts, household electric appliances, vehicle components, building components, various containers, leisure goods/sundries, parts of lighting instruments and the like, parts of various household electrical products and the like, housings, containers, covers, storage portions, or cases of electrical apparatuses, and covers or cases of lighting apparatuses. Examples of the electric and electronic equipment include personal computers, gaming devices, television receivers, display devices such as liquid crystal display devices and plasma display devices, printers, copy machines, scanners, fax machines, electronic organizers and personal digital assistants (PDA), electronic desktop calculators, electronic dictionaries, cameras, video cameras, cellular phones, cell packs, drives and readout devices for storage media, mouse, numeric keypads, compact disc (CD) players, minidisc (MD) players, and portable radios/audio players. Furthermore, examples of the molded article include electric signboards, liquid crystal backlights, illumination displays, traffic signs, signboards, screens, vehicle components such as light reflectors and meter parts, toys, and accessories.

The method for producing the molded article according to an embodiment of the present invention is not particularly limited, and any molding method generally used for polycarbonate resin compositions can be employed. Examples thereof include injection molding methods, ultrahigh-speed injection molding methods, injection compression molding methods, two-color molding methods, blow molding methods such as gas assisted molding, molding methods using a heat insulating mold, molding methods using a rapid heating mold, foam molding (including supercritical fluid), insert molding, in-mold coating molding (IMC) methods, extrusion molding methods, sheet molding methods, heat molding methods, rotational molding methods, lamination molding methods, and press molding methods. In addition, a molding method using a hot runner system can also be used.

Examples

The present invention is described more specifically below through examples. The materials, used amounts, proportions, processing contents, processing procedures, and the like described in the examples below may be changed as appropriate, unless the spirit of the present invention is departed. Therefore, the scope of the present invention is not limited to the specific examples described below.

Synthesis of End-Capping Agent: Synthesis of 6-ethynyl-2-naphthol (6E2Nap)

The synthesis was performed according to the following scheme.

[Chemical Formula 22]

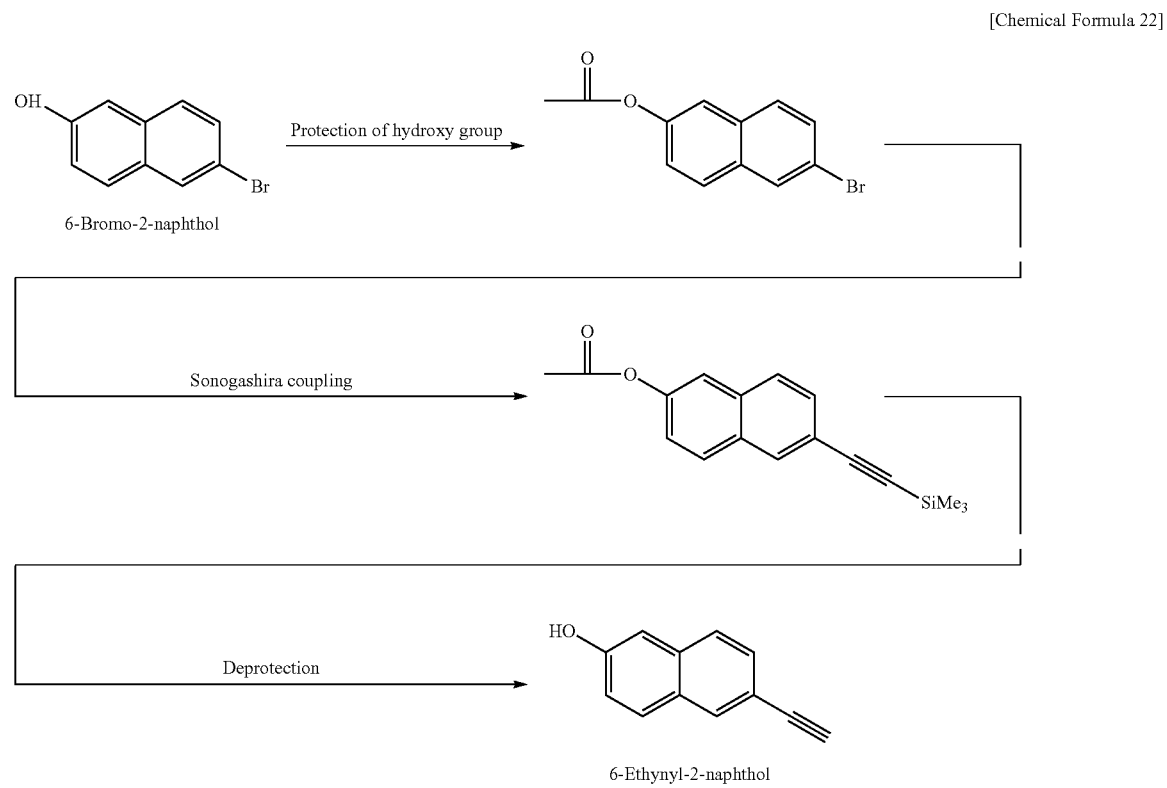

In a 300 mL three-necked flask equipped with a Dimroth condenser and a stirrer, 20.00 g (89.66 mol) of 6-bromo-2-napthol and 100 mL of acetic anhydride were charged and reacted at 150° C. for 2 hours under a nitrogen stream. The reaction product was cooled down to room temperature and neutralized by a sodium bicarbonate solution. Then, the mixture was poured into water, and precipitated white precipitate was collected. The precipitate was dried under reduced pressure at 60° C. for 3 hours to obtain (6-bromo-2-naphthyl)acetate. Yield in grams was 15.56 g (percent yield: 65.5%).

In a 500 mL three-necked flask equipped with a Dimroth condenser and a stirrer, 3.79 g (14.3 mmol) of (6-bromo-2-naphthyl)acetate synthesized as described above, 5.62 g (57.2 mmol) of trimethylsilylacetylene, 200 mL of tetrahydrofuran, and 50 mL of triethylamine were charged and agitated under a nitrogen stream. 1.72 g (1.49 mmol) of tetrakis(triphenylphosphine)palladium and 0.53 g (2.78 mmol) of copper iodide were added thereinto and reacted at room temperature for 16 hours while the mixture was shielded from the light.

After completion of the reaction, the solvent was removed using an evaporator. Then, the reactant was extracted with 200 mL of diethyl ether, and was washed with distilled water. The organic layer was dehydrated with anhydrous magnesium sulfate, and the solvent was removed using the evaporator. The residue was purified by column chromatography using a mixed solvent of hexane/acetone (6/1). (6-Trimethylsilylethynyl-2-naphthyl)acetate in a form of white powders was obtained (3.66 g (percent yield: 90.6%)).

The trimethylsilyl group and acetyl group were removed from the obtained compound. In a 300 mL flask, the ester was charged, and the flask was purged with nitrogen. 3.5 g of sodium hydrogencarbonate, 40 mL of methanol, 40 mL of tetrahydrofuran, and 60 mL of water were added thereinto and agitated at 55° C. for 12 hours. The reaction mixture was diluted with 150 mL of water, and the reactant was extracted with 40 mL of diethyl ether for five times. The reaction mixture was dried with magnesium sulfate, filtered, concentrated using an evaporator, and purified by column chromatography using a mixed solvent of hexane/acetone (3/1). The obtained light brown powder was dried under reduced pressure at room temperature for 3 hours to obtain the title compound (percent yield: 71%).

$^1$H-NMR (400 MHz, CDCl$_3$, ppm): δ=7.95; (s, 1H), 7.70; (d, 1H), 7.61; (d, 1H), 7.47; (d, 1H), 7.12; (m, 2H), 5.20; (s, 1H), 3.11; (s, 1H).

Synthesis of End-Capping Agent: Synthesis of 6-phenylethynyl-2-naphthol (6PE2Nap)

The synthesis was performed according to the following scheme.

[Chemical Formula 23]

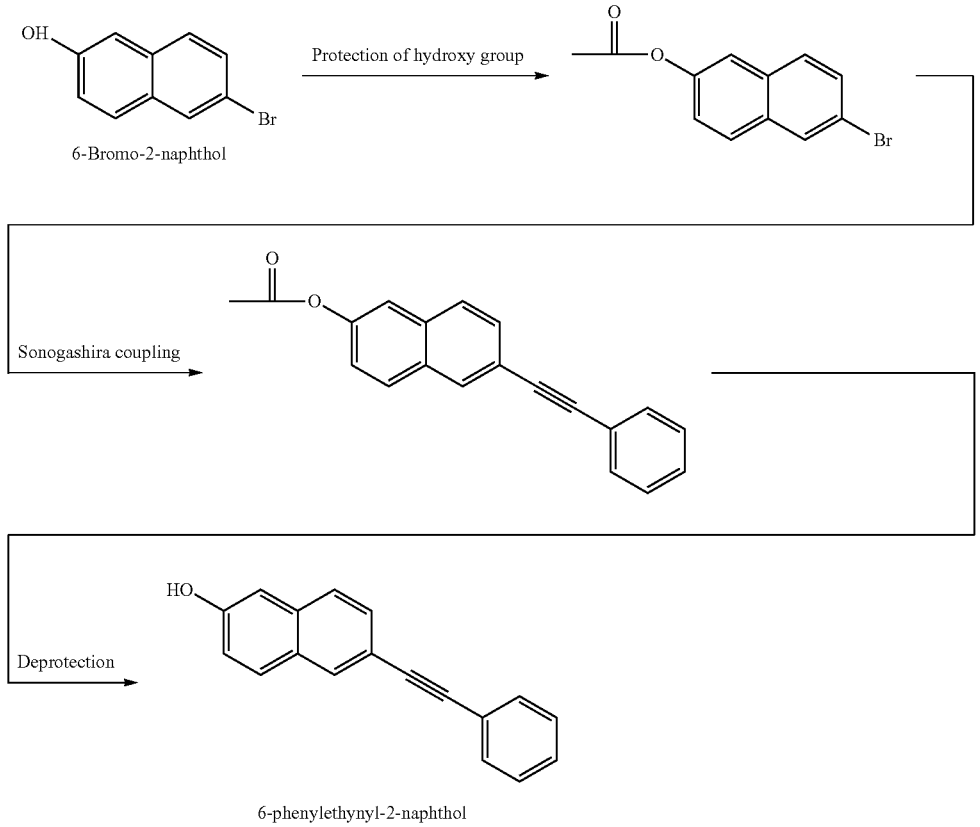

6-phenylethynyl-2-naphthol

In a 500 mL three-necked flask equipped with a Dimroth condenser and a stirrer, 3.79 g (14.3 mmol) of (6-bromo-2-naphthyl)acetate, 5.84 g (57.2 mmol) of phenylacetylene, 200 mL of tetrahydrofuran, and 50 mL of triethylamine were charged and agitated under a nitrogen stream. 1.72 g (1.49 mmol) of tetrakis(triphenylphosphine)palladium and 0.53 g (2.78 mmol) of copper iodide were added thereinto and reacted at room temperature for 16 hours while the mixture was shielded from the light.

After completion of the reaction, the solvent was removed using an evaporator. Then, the reactant was extracted with 200 mL of diethyl ether, and was washed with distilled water. The organic layer was dehydrated with anhydrous magnesium sulfate, and the solvent was removed using the evaporator. The residue was purified by column chromatography using a mixed solvent of hexane/acetone (6/1). (6-phenylethynyl-2-naphthyl)acetate in a form of white powders was obtained (0.96 g (percent yield: 23.4%)).

The acetyl group was removed from the obtained compound. In a 300 mL flask, 0.96 g (3.35 mmol) of the ester was charged, and the flask was purged with nitrogen. 2.5 g of sodium hydrogencarbonate, 25 mL of methanol, 25 mL of tetrahydrofuran, and 35 mL of water were added thereinto and agitated at 55° C. for 12 hours. The reaction mixture was diluted with 100 mL of water, and the reactant was extracted with 40 mL of diethyl ether for five times. The reaction mixture was dried with magnesium sulfate, filtered, concentrated using an evaporator, and purified by column chromatography using a mixed solvent of hexane/acetone (3/1). The obtained light brown powder was dried under reduced pressure at room temperature for 3 hours to obtain the title compound (percent yield: 42%).

$^1$H-NMR (400 MHz, CDCl$_3$, ppm): δ=7.98; (s, 1H), 7.73; (d, 1H), 7.63; (d, 1H), 7.55; (m, 3H), 7.35; (m, 3H), 7.13; (m, 2H), 5.15; (s, 1H).

Synthesis of
6-(3,5-dimethoxyphenyl)ethynyl-2-naphthol

In a 500 mL three-necked flask equipped with a Dimroth condenser and a stirrer, 0.33 g (1.24 mmol) of (6-bromo-2-naphthyl)acetate, 0.81 g (4.99 mmol) of 1-ethynyl-3,5-dimethoxybenzene, 20 mL of tetrahydrofuran, and 5 mL of triethylamine were charged and agitated under a nitrogen stream. 0.15 g (0.13 mmol) of tetrakis(triphenylphosphine) palladium and 0.046 g (0.24 mmol) of copper iodide were added thereinto and heated to reflux for 16 hours while the mixture was shielded from the light.

After completion of the reaction, the solvent was removed using an evaporator. Then, the reactant was extracted with 50 mL of diethyl ether, and was washed with distilled water. The organic layer was dehydrated with anhydrous magnesium sulfate, and the solvent was removed using the evaporator. The residue was purified by column chromatography using a mixed solvent of hexane/acetone (5/1). (6-(3,5-Dimethoxyphenyl)ethynyl-2-naphthyl)acetate in a form of white powders was obtained (0.05 g (percent yield: 11.6%)).

The acetyl group was removed from the obtained compound. In a 30 mL flask, 0.035 g (0.1 mmol) of the ester was charged, and the flask was purged with nitrogen. 0.1 g of sodium hydrogencarbonate, 1 mL of methanol, 1 mL of tetrahydrofuran, and 1.5 mL of water were added thereinto and agitated at 55° C. for 12 hours. The reaction mixture was diluted with 2 mL of water, and the reactant was extracted with 10 mL of diethyl ether for five times. The reaction mixture was dried with magnesium sulfate, filtered, concentrated using an evaporator, and purified by column chromatography using a mixed solvent of hexane/acetone (3/1). The obtained light brown powder was dried under reduced pressure at room temperature for 3 hours to obtain the title compound (percent yield: 11%).

$^1$H-NMR (400 MHz, CDCl$_3$, ppm): δ=7.99; (s, 1H), 7.73; (d, 1H), 7.61; (d, 1H), 7.54; (d, 1H), 7.12; (m, 2H), 6.72; (d, 2H), 6.47; (s, 1H), 5.03; (s, 1H), 3.82; (s, 6H).

Synthesis of Polycarbonate End-Capped with
6-phenylethynyl-2-naphthol (PC-A)

In 550 mL of 9 mass % sodium hydroxide solution, 73.4 g (0.32 mol) of 2,2-bis(4-hydroxyphenyl)propane (hereinafter, abbreviated as "BPA"; available from Shin-Nittetsu Kagaku Kogyo K.K.) and 0.6 g of hydrosulfite were dissolved. 250 mL of dichloromethane was added thereinto, and while the solution temperature was maintained in a range of 15° C. to 25° C. under agitation, 43 g of phosgene was blown therein for approximately 30 minutes.

After the completion of blowing of the phosgene, 100 mL of 9 mass % sodium hydroxide solution, 100 mL dichloromethane, and a solution, in which 3.02 g (0.012 mol) of the 6-phenylethynyl-2-naphthol as an end-capping agent was dissolved in 100 mL of dichloromethane, were added. Then, after the mixture was vigorously agitated to be emulsified, 0.4 mL of triethylamine was added and agitated at from 20 to 27° C. for approximately 40 minutes for polymerization.

After the completion of the polymerization, the reaction solution was separated into an aqueous phase and an organic phase. The organic phase was neutralized with phosphoric acid and repeatedly washed with water until the electric conductivity of the wash liquid (aqueous phase) became 10 μS/cm or less. The organic solvent was removed by distillation from the purified polycarbonate resin solution to obtain a polycarbonate resin powder. The viscosity average molecular weight Mv of the obtained polycarbonate resin was 22900.

Synthesis of Polycarbonate End-Capped with
6-ethynyl-2-naphthol (PC-B)

In 750 mL of 9 mass % sodium hydroxide solution, 105.4 g (0.46 mol) of BPA (available from Shin-Nittetsu Kagaku Kogyo K.K.) and 0.6 g of hydrosulfite were dissolved. 350 mL of dichloromethane was added thereinto, and while the solution temperature was maintained in a range of 15° C. to 25° C. under agitation, 62 g of phosgene was blown therein for approximately 40 minutes. After the completion of blowing of the phosgene, 100 mL of 9 mass % sodium hydroxide solution, 200 mL dichloromethane, and a solution, in which 2.98 g (0.018 mol) of the 6-ethynyl-2-naphthol as an end-capping agent was dissolved in 100 mL of dichloromethane, were added. Then, after the mixture was vigorously agitated to be emulsified, 0.4 mL of triethylamine was added and agitated at from 20 to 27° C. for approximately 40 minutes for polymerization.

After the completion of the polymerization, the reaction solution was separated into an aqueous phase and an organic phase. The organic phase was neutralized with phosphoric acid and repeatedly washed with water until the electric conductivity of the wash liquid (aqueous phase) became 10 μS/cm or less. The organic solvent was removed by distillation from the purified polycarbonate resin solution to obtain a polycarbonate resin powder. The viscosity average molecular weight Mv of the obtained polycarbonate resin was 21600.

Synthesis of Polycarbonate End-Capped with p-t-butylphenol (PC-C)

In 640 mL of 9 mass % sodium hydroxide solution, 100 g (0.44 mol) of BPA (available from Shin-Nittetsu Kagaku Kogyo K.K.) and 0.6 g of hydrosulfite were dissolved. 360 mL of dichloromethane was added thereinto, and while the solution temperature was maintained in a range of 15° C. to 25° C. under agitation, 57 g of phosgene was blown therein for approximately 40 minutes. After the completion of blowing of the phosgene, 100 mL of 9 mass % sodium hydroxide solution, 100 mL dichloromethane, and a solution, in which 2.72 g (0.018 mol) of the p-t-butylphenol as an end-capping agent was dissolved in 100 mL of dichloromethane, were added. Then, after the mixture was vigorously agitated to be emulsified, 0.4 mL of triethylamine was added and agitated at from 20 to 27° C. for approximately 40 minutes for polymerization.

After the completion of the polymerization, the reaction solution was separated into an aqueous phase and an organic phase. The organic phase was neutralized with phosphoric acid and repeatedly washed with water until the electric conductivity of the wash liquid (aqueous phase) became 10 $\mu$S/cm or less. The organic solvent was removed by distillation from the purified polycarbonate resin solution to obtain a polycarbonate resin powder. The viscosity average molecular weight Mv of the obtained polycarbonate resin was 21300.

Synthesis of Polycarbonate End-Capped with p-phenylethynylphenol (PC-D)

A polycarbonate resin having a terminal p-phenylethynylphenol group was synthesized in accordance with the description of paragraph 0067 of JP 2014-051538 A.

Other Additives

Flame retardant: potassium perfluorobutane sulfonate; trade name: MEGAFACE F-114P, available from DIC Corporation Stabilizer: tris(2,4-di-tert-butylphenyl)phosphite; trade name: ADK STAB 2112, available from Adeka Corporation Mold release agent 1: pentaerythritol tetrastearate; trade name: LOXIOL VPG 861, available from Cognis Japan Ltd.

Mold release agent 2: octadecyl stearate; trade name: UNISTAR M9676, available from NOF Corporation

Examples 1 to 4 and Comparative Examples 1 to 4

The polycarbonate resin compositions of Examples 1 to 4 and Comparative Examples 1 to 4 were prepared by the method described below. That is, components were mixed in contents (parts by mass) shown in Table 1 and then kneaded for 3 minutes using a Labo Plastomill (30C150, available from Toyo Seiki Seisaku-sho, Ltd.) at a screw rotation of 60 rpm and a mixer temperature of 260° C. The resin lump collected after the kneading was crushed into a pellet shape having a diameter of 6 mm or smaller by using a miller (Orient Mill VM-16; available from Seishin Enterprise Co., Ltd.) to obtain a sample of the polycarbonate resin composition.

Molding of Test Piece 1

In the transparency (haze) and hue (YI) tests, the obtained sample was dried at 120° C. for 5 hours, and then injection molding was performed by using a tabletop injection molding machine (MiniJet, available from HAAKE) at a cylinder temperature of 300° C., a mold temperature of 100° C., a preheating time of 3 minutes, and an injection pressure of 900 mb to mold a plate-like molded article having a length of 50 mm, a width of 30 mm, and a thickness of 1.0 mm as a test piece 1.

Molding of Test Piece 2

In the flame retardancy (LOI) test, the obtained sample was dried at 120° C. for 5 hours, and then injection molding was performed by using a tabletop injection molding machine (MiniJet, available from HAAKE) at a cylinder temperature of 300° C., a mold temperature of 100° C., a preheating time of 3 minutes, and an injection pressure of 900 mb to mold an Izod molded article as a test piece 2.

Transparency Evaluation: Haze (Haze Value) (Unit: %)

In accordance with JIS K-7105, the haze value (unit: %) was measured for the test piece 1 (1 mm thick) as a test piece by a haze meter, model NDH-2000, available from Nippon Denshoku Industries Co., Ltd. Haze is a value used as a measure of the turbidity of the resin, and a smaller value indicates a higher transparency and is preferred. The results are shown in Table 1. Note that, in the table, this is denoted as "Haze".

Hue Evaluation: YI Value

In accordance with JIS K-7105, the Yellow Index (YI) value was measured for the test piece 1 (1 mm thick) as a test piece employing the transmission method using a spectrocolorimeter, model SE2000, available from Nippon Denshoku Industries Co., Ltd. A smaller YI value indicates a lower degree of yellowness of the resin and is preferred. The results are shown in Table 1. Note that, in the table, this is denoted as "YI".

Heat Resistance Evaluation: Glass Transition Temperature (Tg) (Unit: ° C.)

For the obtained polycarbonate resin composition, Tg was measured in accordance with JIS K 7121 by using a high-sensitivity differential scanning calorimeter, model DSC 7020, available from SII NanoTechnology Inc. A larger value of Tg indicates superior heat resistance and is preferred. The results are shown in Table 1. Note that, in the table, this is denoted as "Tg".

Flame Retardancy Evaluation: LOI (Unit: %)

The test piece 2 (Izod test piece) molded as described above was acclimated in a thermostatic chamber at a temperature of 23° C. and a relative humidity of 50% for 48 hours. The test was performed in accordance with JIS K 7201 "Determination of burning behavior of polymeric material by oxygen index". In this test, the test piece having an oxygen index (LOI value) at burning of 26 or greater can be rated as flame retardant (self-extinguishing property). Note that, in the table, this is denoted as "LOI".

Flame Retardancy Evaluation: UL94 Test

The polycarbonate resin composition obtained as described above was subjected to injection-molding by using an injection molding machine ("SE 50 DUZ", available from Sumitomo Heavy Industries, Ltd.) at a cylinder temperature of 300° C. and a mold temperature of 120° C. to form each test piece for burning that had a size of 12.5 mm×125 mm and a thickness of 3.2 mm, 1.6 mm, or 0.8 mm. Evaluation of the flame retardancy was performed as follows.

Flame Retardancy (UL94)

In accordance with the method of Subject 94 (UL94) of Underwriters Laboratories, five test pieces were tested for the fire retardancy and classified into V-0, V-1, V-2, and inadequate (NG).

Furthermore, the longest burning time for two ignition processes (unit: second) and the total burning time for two ignition processes (unit: second) were measured. The measurement was performed for five times for each test piece, and the result was shown as the average value thereof. Furthermore, for the test piece that had shown sagging, the result was recorded as "sagging".

The obtained measurement results of Examples 1 to 4 and Comparative Example 1 to Comparative Example 4 were shown in Table 1 below.

TABLE 1

| | | Example 1 | Example 2 | Example 3 | Example 4 |
|---|---|---|---|---|---|
| Polycarbonate resin | PC-A | 100 | | | 50 |
| | PC-B | | 100 | 100 | 50 |
| | PC-C | | | | |
| | PC-D | | | | |
| Additive | Flame retardant | | | 0.1 | 0.1 |
| | Stabilizer | 0.03 | 0.03 | 0.03 | 0.03 |
| | Mold release agent 1 | 0.1 | 0.1 | 0.1 | 0.1 |
| | Mold release agent 2 | 0.1 | 0.1 | 0.1 | 0.1 |
| Haze (%) | Transparency | 0.8 | 0.9 | 0.9 | 0.6 |
| YI | Hue | 6 | 8 | 8 | 4 |
| Tg (° C.) | Heat resistance | 164 | 152 | 153 | 155 |
| LOI (%) | Flame retardancy | 42 | 42 | 44 | 43 |
| UL94 Test | Flammability (3.2 mm thick) | V-0 | V-0 | V-0 | V-0 |
| | Longest burning time for two ignition processes for each of the five test pieces (s) | 3 | 3 | 1 | 2 |
| | Total burning time for two ignition processes for each of the five test pieces (s) | 9 | 10 | 5 | 7 |
| | Flammability (1.6 mm thick) | Unmoldable | V-2 | V-0 | V-0 |
| | Longest burning time for two ignition processes for each of the five test pieces (s) | | 3 | 2 | 2 |
| | Total burning time for two ignition processes for each of the five test pieces (s) | | 23 | 6 | 10 |
| | | | Sagging | | |
| | Flammability (0.8 mm thick) | Unmoldable | V-2 | V-0 | V-0 |
| | Longest burning time for two ignition processes for each of the five test pieces (s) | | 8 | 1 | 2 |
| | Total burning time for two ignition processes for each of the five test pieces (s) | | 30 | 5 | 9 |
| | | | Sagging | | |

| | | Comparative Example 1 | Comparative Example 2 | Comparative Example 3 | Comparative Example 4 |
|---|---|---|---|---|---|
| Polycarbonate resin | PC-A | | | | |
| | PC-B | | | | |
| | PC-C | 100 | 100 | | |
| | PC-D | | | 100 | 100 |
| Additive | Flame retardant | | 0.1 | | 0.1 |
| | Stabilizer | 0.03 | 0.03 | 0.03 | 0.03 |
| | Mold release agent 1 | 0.1 | 0.1 | 0.1 | 0.1 |
| | Mold release agent 2 | 0.1 | 0.1 | 0.1 | 0.1 |
| Haze (%) | Transparency | 0.5 | 0.5 | 0.8 | 0.8 |
| YI | Hue | 1 | 2 | 8 | 8 |
| Tg (° C.) | Heat resistance | 150 | 149 | 150 | 149 |
| LOI (%) | Flame retardancy | 26 | 38 | 30 | 41 |
| UL94 Test | Flammability (3.2 mm thick) | NG | V-2 | V-2 | V-1 |
| | Longest burning time for two ignition processes for each of the five test pieces (s) | 47 | 20 | 15 | 15 |
| | Total burning time for two ignition processes for each of the five test pieces (s) | 147 | 100 | 90 | 80 |
| | | | Sagging | Sagging | |
| | Flammability (1.6 mm thick) | V-2 | V-2 | V-2 | V-2 |

TABLE 1-continued

| | | | | |
|---|---|---|---|---|
| Longest burning time for two ignition processes for each of the five test pieces (s) | 12 | 15 | 15 | 10 |
| Total burning time for two ignition processes for each of the five test pieces (s) | 70 | 45 | 50 | 51 |
| | Sagging | Sagging | Sagging | Sagging |
| Flammability (0.8 mm thick) | V-2 | V-2 | V-2 | V-2 |
| Longest burning time for two ignition processes for each of the five test pieces (s) | 8 | 3 | 5 | 3 |
| Total burning time for two ignition processes for each of the five test pieces (s) | 53 | 30 | 45 | 25 |
| | Sagging | Sagging | Sagging | Sagging |

As is clear from the results described above, in each of the cases where the polycarbonate resin compositions according to an embodiment of the present invention were used (Examples 1 to 4), the obtained polycarbonate resin composition has excellent flame retardancy and high heat resistance. Furthermore, the transparency and the hue thereof were also excellent. In particular, the polycarbonate resin compositions were highly valuable from the viewpoint of achieving V-0 even without blending any flame retardant (Examples 1 and 2). Furthermore, in Example 1, a molded article having a low thickness was not obtained. That is, the moldability was superior in Examples 2 to 4 compared to that of Example 1.

On the contrary, in each of the cases where the polycarbonate resin compositions that were not in the scope of the present invention (Comparative Examples 1 to 4) were used, the heat resistance and the flame retardancy were inferior.

The invention claimed is:

1. A polycarbonate resin composition comprising:
   a polycarbonate resin having a terminal structure represented by Formula (A) and having a viscosity average molecular weight from $1 \times 10^4$ to $5 \times 10^4$, and
   a stabilizer;

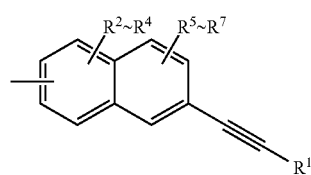

Formula (A)

wherein, $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

2. The polycarbonate resin composition according to claim 1, wherein Formula (A) is represented by Formula (B):

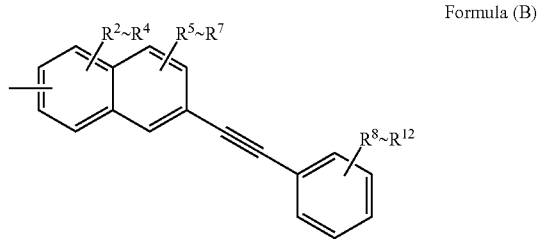

Formula (B)

wherein, $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

3. The polycarbonate resin composition according to claim 1, wherein Formula (A) is represented by Formula (C):

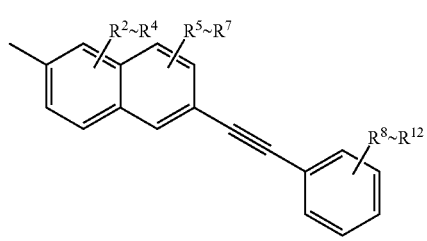

Formula (C)

wherein, $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

4. The polycarbonate resin composition according to claim 1, wherein the stabilizer is at least one type selected from the group consisting of thermal stabilizers and antioxidants.

5. The polycarbonate resin composition of claim 1, wherein the polycarbonate resin has a Tg of 151° C. or higher.

6. A polycarbonate resin having a terminal structure represented by Formula (A) and having a viscosity average molecular weight from $1 \times 10^4$ to $5 \times 10^4$;

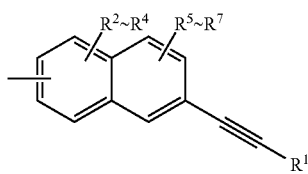

Formula (A)

wherein, $R^1$ is selected from the group consisting of a hydrogen atom, halogen atoms, linear alkyl groups having from 1 to 9 carbons, branched alkyl groups having from 3 to 9 carbons, linear alkenyl groups having from 2 to 9 carbons, branched alkenyl groups having from 3 to 9 carbons, and aryl groups having from 6 to 12 carbons; and $R^2$ to $R^7$ are each independently selected from the group consisting of a hydrogen atom, alkyl groups having from 1 to 9 carbons, and alkoxy groups having from 1 to 9 carbons.

7. A molded article formed from the polycarbonate resin composition described in claim 1.

8. The polycarbonate resin of claim 6 having a Tg of 151° C. or higher.

9. The polycarbonate resin according to claim 6, wherein Formula (A) is represented by Formula (B):

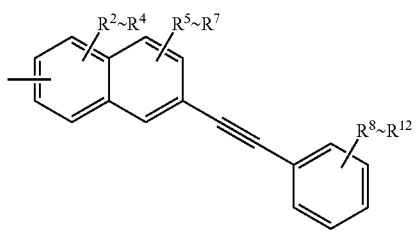

Formula (B)

wherein, $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

10. The polycarbonate resin according to claim 6, wherein Formula (A) is represented by Formula (C):

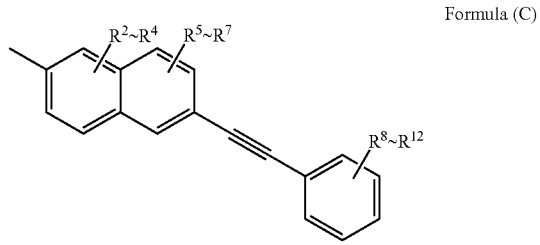

Formula (C)

wherein, $R^2$ to $R^7$ are each independently selected from the group consisting of a hydrogen atom, alkyl groups having from 1 to 9 carbons, and alkoxy groups having from 1 to 9 carbons; and $R^8$ to $R^{12}$ are each independently selected from the group consisting of a hydrogen atom, alkyl groups having from 1 to 9 carbons, and alkoxy groups having from 1 to 9 carbons.

* * * * *